United States Patent
Avisar et al.

(10) Patent No.: US 10,943,505 B2
(45) Date of Patent: Mar. 9, 2021

(54) HYBRID IMAGE/SCENE RENDERER WITH HANDS FREE CONTROL

(71) Applicant: Surgical Theater, Inc., Mayfield Village, OH (US)

(72) Inventors: Mordechai Avisar, Highland Heights, OH (US); Alon Yakob Geri, Orange Village, OH (US)

(73) Assignee: SURGICAL THEATER, INC., Mayfield Village, OH (US)

( * ) Notice: Subject to any disclaimer, the term of this patent is extended or adjusted under 35 U.S.C. 154(b) by 73 days.

(21) Appl. No.: 16/033,937

(22) Filed: Jul. 12, 2018

(65) Prior Publication Data

US 2018/0322806 A1   Nov. 8, 2018

Related U.S. Application Data

(63) Continuation of application No. 14/402,746, filed as application No. PCT/US2013/042654 on May 24, 2013, now Pat. No. 10,056,012.
(Continued)

(51) Int. Cl.
*G09B 23/28* (2006.01)
*G06F 3/01* (2006.01)
(Continued)

(52) U.S. Cl.
CPC .......... *G09B 23/28* (2013.01); *A61B 17/1227* (2013.01); *A61B 34/10* (2016.02);
(Continued)

(58) Field of Classification Search
CPC ...... G09F 3/016; G09F 3/048; G06F 19/3437; G06F 19/3481; G09B 23/28; G09B 23/285; G09B 23/30
See application file for complete search history.

(56) References Cited

U.S. PATENT DOCUMENTS

| 5,595,703 A | 1/1997 | Swaelens et al. |
| 5,768,134 A | 6/1998 | Swaelens et al. |

(Continued)

FOREIGN PATENT DOCUMENTS

| CN | 1720561 A | 1/2006 |
| CN | 1973780 A | 6/2007 |

(Continued)

OTHER PUBLICATIONS

Montgomery, K. et al; Studies in Health Technology and Informatics; "Spring: A General Framework for Collaborative, Real-time Surgical Simulation"; 2002, vol. 85, pp. 296-303.
(Continued)

*Primary Examiner* — Robert J Utama
(74) *Attorney, Agent, or Firm* — Bodi Law LLC

(57) ABSTRACT

A system and method for converting static/still medical images of a particular patient into dynamic and interactive images interacting with medical tools including medical devices by coupling a model of tissue dynamics and tool characteristics to the patient specific imagery for simulating a medical procedure in an accurate and dynamic manner by coupling a model of tissue dynamics to patient specific imagery for simulating surgery on the particular patient. The method includes a tool to add and/or to adjust the dynamic image of tissues and ability to draw any geometric shape on the dynamic image of tissues and to add the shape into the modeling system.

28 Claims, 16 Drawing Sheets
(12 of 16 Drawing Sheet(s) Filed in Color)

Related U.S. Application Data

(60) Provisional application No. 61/651,775, filed on May 25, 2012.

(51) Int. Cl.

| | | |
|---|---|---|
| *A61B 17/122* | (2006.01) | |
| *A61B 34/10* | (2016.01) | |
| *G16H 50/50* | (2018.01) | |
| *G06F 19/00* | (2018.01) | |
| *A61B 17/12* | (2006.01) | |
| *A61B 17/128* | (2006.01) | |
| *A61B 17/00* | (2006.01) | |

(52) U.S. Cl.
CPC .............. *G06F 3/016* (2013.01); *G06F 19/00* (2013.01); *G16H 50/50* (2018.01); *A61B 17/12* (2013.01); *A61B 17/1285* (2013.01); *A61B 2017/00707* (2013.01); *A61B 2034/104* (2016.02)

(56) References Cited

U.S. PATENT DOCUMENTS

| | | | |
|---|---|---|---|
| 5,826,206 | A | 10/1998 | Nemeth |
| 6,037,927 | A | 3/2000 | Rosenberg |
| 6,113,395 | A | 9/2000 | Hon |
| 6,847,336 | B1 | 1/2005 | Lemelson et al. |
| 6,857,878 | B1 | 2/2005 | Chosack et al. |
| 6,863,536 | B1 | 3/2005 | Fisher et al. |
| 6,939,138 | B2 | 9/2005 | Chosack et al. |
| 7,101,383 | B1 | 9/2006 | Van Ess |
| 7,261,565 | B2 | 8/2007 | Chosack et al. |
| 7,616,730 | B2 | 11/2009 | Flohr |
| 8,311,791 | B1 | 11/2012 | Avisar |
| 8,504,136 | B1 | 8/2013 | Sun et al. |
| 9,788,905 | B2 | 10/2017 | Avisar |
| 2001/0046935 | A1 | 11/2001 | Okamura |
| 2002/0059284 | A1 | 5/2002 | Bronstein et al. |
| 2004/0009459 | A1* | 1/2004 | Anderson ........... G06F 19/3481 434/262 |
| 2004/0253572 | A1 | 12/2004 | Chosack et al. |
| 2005/0032028 | A1 | 2/2005 | Chosack et al. |
| 2006/0036167 | A1 | 2/2006 | Shina |
| 2006/0082542 | A1 | 4/2006 | Morita et al. |
| 2006/0085175 | A1 | 4/2006 | Hartlep et al. |
| 2006/0281971 | A1 | 12/2006 | Sauer |
| 2007/0129626 | A1 | 6/2007 | Mahesh et al. |
| 2007/0134637 | A1 | 6/2007 | Bronstein et al. |
| 2007/0141543 | A1 | 6/2007 | Grund-Pedersen |
| 2007/0248261 | A1 | 10/2007 | Zhou et al. |
| 2009/0018808 | A1 | 1/2009 | Bronstein et al. |
| 2009/0187393 | A1 | 7/2009 | Van Lierde et al. |
| 2009/0311655 | A1* | 12/2009 | Karkanias ........... G09B 23/28 434/262 |
| 2010/0009314 | A1 | 1/2010 | Tardieu et al. |
| 2010/0092904 | A1 | 4/2010 | Esposti et al. |
| 2010/0161076 | A1 | 6/2010 | Pallari |
| 2010/0178644 | A1 | 7/2010 | Meglan et al. |
| 2010/0191088 | A1 | 7/2010 | Anderson et al. |
| 2010/0217336 | A1 | 8/2010 | Crawford et al. |
| 2010/0305928 | A1 | 12/2010 | Cohen et al. |
| 2011/0236868 | A1 | 9/2011 | Bronstein et al. |
| 2011/0238395 | A1 | 9/2011 | Kubota et al. |
| 2012/0058457 | A1 | 3/2012 | Savitsky |
| 2013/0034282 | A1* | 2/2013 | Kaufman ........... G06T 7/0014 382/128 |
| 2013/0047103 | A1 | 2/2013 | Avisar |
| 2013/0267838 | A1 | 10/2013 | Fronk et al. |
| 2014/0088941 | A1 | 3/2014 | Banerjee et al. |
| 2018/0092698 | A1 | 4/2018 | Chopra et al. |

FOREIGN PATENT DOCUMENTS

| | | |
|---|---|---|
| CN | 102354345 A | 2/2012 |
| EP | 1 395 194 A1 | 3/2004 |
| JP | 2006509238 A | 3/2006 |
| JP | 2006223374 | 8/2006 |
| JP | 2010131047 | 6/2010 |
| JP | 2014522248 | 9/2014 |
| JP | 2014525764 | 10/2014 |
| WO | WO9610949 | 4/1996 |
| WO | WO 02/100284 A1 | 12/2002 |
| WO | 2004029908 A1 | 4/2004 |
| WO | 2004051603 A1 | 6/2004 |
| WO | WO2004051603 | 6/2004 |
| WO | WO 2008/076079 A1 | 6/2008 |
| WO | 2009059716 A1 | 5/2009 |
| WO | WO2009059716 | 5/2009 |
| WO | 2009094621 A2 | 7/2009 |
| WO | 2010030523 A1 | 3/2010 |
| WO | WO2010106532 A1 | 9/2010 |
| WO | 2010132606 A1 | 11/2010 |
| WO | WO 2012/033739 A1 | 3/2012 |
| WO | 2012135653 A1 | 10/2012 |
| WO | 2013177520 A1 | 11/2013 |
| WO | 2015154069 A1 | 10/2015 |

OTHER PUBLICATIONS

Qin, J. et al; Studies in Health Technology and Informatics; "An Adaptive Framework Using Cluster-Based Hybrid Architecture for Enhancing Collaboration in Surgical Simulation"; 2007, vol. 125, pp. 367-372.

MedGadget (Surgical Navigation Advanced Plaffform (SNAP) for Intra-Op Visualization of Patient's Brain, https://www.medgadget.co rn/2014/07 /surg i cal-n avigation-advanced-plaffor rnsnap-for-intra-op-visual izati on-of-patients-brain. ht ml, Jul. 3, 2014).II.

Reitinger et al. "Liver Surgery Planning using Virtual Reality" IEEE Computer Graphics and Applications.

State Intellectual Property Office; Search Report; 1st Search; Application No. 2013850022805X; Applicant: Surgical Theater LLC; Date of Search Completion: Jul. 20, 2016.

J Neurosurg vol. 93; Relevant Pages: pp. 355-369 and Figures 3, 4, 6 and 8; Date of Issuance: Aug. 31, 2000; Title of Article: "Simulation of the surgical manipulation involved in clipping a basilar artery aneurysm: concepts of virtual clipping"; Author and Publisher: Toru Koyama, M.D. et al.; Department of Neurosurgery, Shinshu University School of Medicine Matsumoto, Japan.

Bornik A et al: "Computer Aided Liver Surgery Planni ng: An Augmented Reality Approach" Visual Communications and Image Processing; vol. 5029, Feb. 15, 2003, pp. 395-406.

Reitinger, et al: "Liver Surgery Planning Using Virtual Reality"; Virtual and Augmented Reality Supported Similators; IEEE Computer Society; Nov./Dec. 2006.

* cited by examiner

HYBRID IMAGE/SCENE RENDERER WITH HANDS FREE CONTROL

CROSS-REFERENCES TO RELATED APPLICATIONS

This application is a continuation of U.S. patent application Ser. No. 14/402,746 filed on Nov. 21, 2014 and incorporated herein by reference, which is the national phase of International Application No. PCT/US2013/42654 filed on May 24, 2013, the entire disclosure of which is incorporated herein by reference, which claims the benefit of U.S. Provisional Patent Application Ser. No. 61/651,775 which was filed on May 25, 2012 and is incorporated herein by reference

BACKGROUND

This application relates generally to a system and method for simulating surgical procedures. More specifically, this application relates to a system and method for converting static/still medical images into dynamic and interactive images interacting with medical tools (such as, e.g., surgical tools, probes, and/or implantable medical devices) by coupling a model of tissue dynamics to patient specific imagery utilizing hands-free control.

Surgeons lack a rehearsal and preparation tool that would provide them with a realistic visual model with physical tissue properties. Most importantly, it is desired to have a "full immersion" surgical tool that encompasses: (i) realistic "life-like" 2D and/or 3D display of the patient-specific area of surgery (for example—aneurysm); (ii) modeling of the local patient-specific area of surgery geometry and physical properties; (iii) interface enabling manipulation of the patient-specific area of surgery model and virtually perform surgical actions such as cutting, shifting and clamping; and (iv) interface to provide feedback cues to the surgeon.

Furthermore, tools that allow the surgeons to perform simulations using a hands-free control would be useful as well, along with means for correcting deficiencies in, or otherwise modifying, the graphical images of the tissue models.

SUMMARY

Provided are a plurality of example embodiments, including, but not limited to, a modeling system for performing a medical procedure, comprising: a display; an image generator for generating a dynamic image of tissues for display on the display, the generating for displaying on the display the tissues realistically representing corresponding actual biological tissues; a user tool generator for generating a tool model of a user tool for dynamically interacting with the dynamic image of tissues via manipulations provided by a user input for display on the display; and a user interface providing a tool to adjust the dynamic image of tissues displayed on the display by adding or modifying features of the tissues to compensate for anatomical structures that are in the actual biological tissue but are missing from the dynamic image of tissues originally displayed such that the dynamic image of tissues displayed are subsequently displayed on the display with the added or modified features. The tool model is displayed on the display dynamically interacting with the dynamic image of tissues for realistically simulating the medical procedure.

Also provided is a modeling system for enabling a user to perform a simulated medical procedure, the system comprising: one or more computers; a display for displaying images to the user; a database for storing physical characteristics of the tissues of a particular patient; an image generator using one or more of the computers for executing software for generating a dynamic realistic image of the tissues of the particular patient for displaying on the display, wherein the realistic image of the tissues is provided showing an appearance including shadowing and textures indicative of the tissues of the particular patient; a user tool library for providing a plurality of user tool models of actual user tools used in medical procedures; a user interface for accepting inputs from the user for selecting one of the user tool models; a user tool generator using one or more of the computers for executing software for generating a realistic tool image of the selected user tool model for displaying on the display; a user interface for accepting inputs from the user, the inputs for dynamically manipulating the selected user tool image for dynamically interacting with the realistic image of the tissues during the simulated medical procedure for display to the user on the display in real-time; and a user interface providing a tool to adjust the dynamic image of the tissues displayed on the display by adding or modifying features of the tissues for display to compensate for anatomical structures that are in the actual biological tissue of the particular patient but are missing from the dynamic image of tissues originally displayed such that the dynamic image of tissues displayed are subsequently displayed on the display with the added or modified features. The dynamic interaction between the user tool image and the image of the tissues is displayed on the display using images with realistic visual features exhibiting realistic mechanical interactions based on the stored physical characteristics.

Further provided is a modeling system for performing a surgical simulation, comprising: a database for storing patient tissue image information that are taken from, or derived from, medical images of a particular patient; the database also for storing standard characteristics of the tissue; a display; an image generator for generating a dynamic image of tissues of the particular patient for display on the display, the generating utilizing the patient image information such that the dynamic image of tissues is displayed on the display realistically representing corresponding actual tissues of the particular patient; a user tool generator for generating a tool model of a user tool for dynamically interacting with the dynamic image of tissues via manipulations provided by a user for display on the display; and a user interface providing a tool to adjust the dynamic image of tissues displayed on the display by adding or modifying features of the tissues for display to compensate for anatomical structures that are in the actual biological tissue of the particular patient but are missing from the dynamic image of tissues originally displayed such that the dynamic image of tissues displayed are subsequently displayed on the display with the added or modified features. The tool model is displayed on the display dynamically interacting with the dynamic image of tissues for realistically simulating the medical procedure.

Also provided is a modeling system for enabling a user to perform a simulated medical procedure, the system comprising: one or more computers; a display for displaying images to the user; a database for storing characteristics of the tissues of a particular patient; an image generator using one or more of the computers for executing software for generating a dynamic realistic image of the tissues of the particular patient based on the stored characteristics of the particular patient for displaying on the display, wherein the realistic image of the tissues is provided showing an appearance including shadowing and textures indicative of the tissues of the particular patient; a user tool library for providing a plurality of user tool models of actual user tools used in medical procedures; a user interface for accepting inputs from the user for selecting one of the user tool models; a user tool generator using one or more of the computers for executing software for generating a realistic tool image of the selected user tool model for displaying on the display; and a user interface including a camera for accepting hands-free inputs from the user, the inputs for dynamically manipulating the selected user tool image and/or the image of the tissues for dynamically interacting with the realistic image of the tissues during the simulated medical procedure for display to the user on the display in real-time. The dynamic interaction between the user tool image and the image of the tissues is displayed on the display using images with realistic visual features exhibiting realistic mechanical interactions.

Also provided is modeling system for enabling a user to perform a simulated medical procedure, the system comprising: one or more computers; a display for displaying images to the user; an image generator using one or more of the computers for executing software for generating a dynamic realistic image of the tissues for particular patient for displaying on the display, wherein the realistic image of the tissues is provided showing an appearance including shadowing and textures indicative of actual tissues; a database for storing a user tool library for providing a plurality of user tool models of actual user tools used in medical procedures; a user interface for accepting inputs from the user for selecting one of the user tool models; a user tool generator using one or more of the computers for executing software for generating a realistic tool image of the selected user tool model for displaying on the display; and a user interface that can track the motions of an actual surgical instrument being used by the user with the particular patient, such that the motions are used for dynamically manipulating the selected user tool image and/or the image of the tissues for dynamically interacting with the realistic image of the tissues during the simulated medical procedure for display to the user on the display in real-time.

Further provided is a method of performing a surgical simulation, comprising the steps of:
providing a computer system;
providing a display connected to the computer device;
obtaining patient image information about the biological tissues of a particular patient for storing in the computer system;
generating, using the computer system, a dynamic image of the biological tissues of the particular patient for display on the display, the generating utilizing the patient image information such that the dynamic image of tissues is displayed on the display realistically representing corresponding actual tissues of the particular patient;
generating, using the computer system, a user tool model for dynamically interacting with the dynamic image of tissues via manipulations input by a user for display on the display;
adjusting, using a user input to the computer system, the dynamic image of tissues displayed on the display by adding or modifying features of the tissues for display to compensate for anatomical structures that are in the actual biological tissue of the particular patient but are missing from the dynamic image of tissues originally displayed such that the dynamic image of tissues displayed are subsequently displayed on the display with the added or modified features; and
generating, using the computer system, a realistic simulation of the medical procedure for display on the display showing interactions between the dynamic image of tissues and the user tool model according to inputs by the user.

Also provided are additional example embodiments, some, but not all of which, are described hereinbelow in more detail

BRIEF DESCRIPTION OF THE DRAWINGS

The patent or application file contains at least one drawing executed in color. Copies of this patent or patent application publication with color drawings will be provided by the Office upon request and payment of the necessary fee.

The features and advantages of the examples of the present invention described herein will become apparent to those skilled in the art to which the present invention relates upon reading the following description, with reference to the accompanying drawings, in which.

DETAILED DESCRIPTION OF THE EXAMPLE EMBODIMENTS

Figure 1:
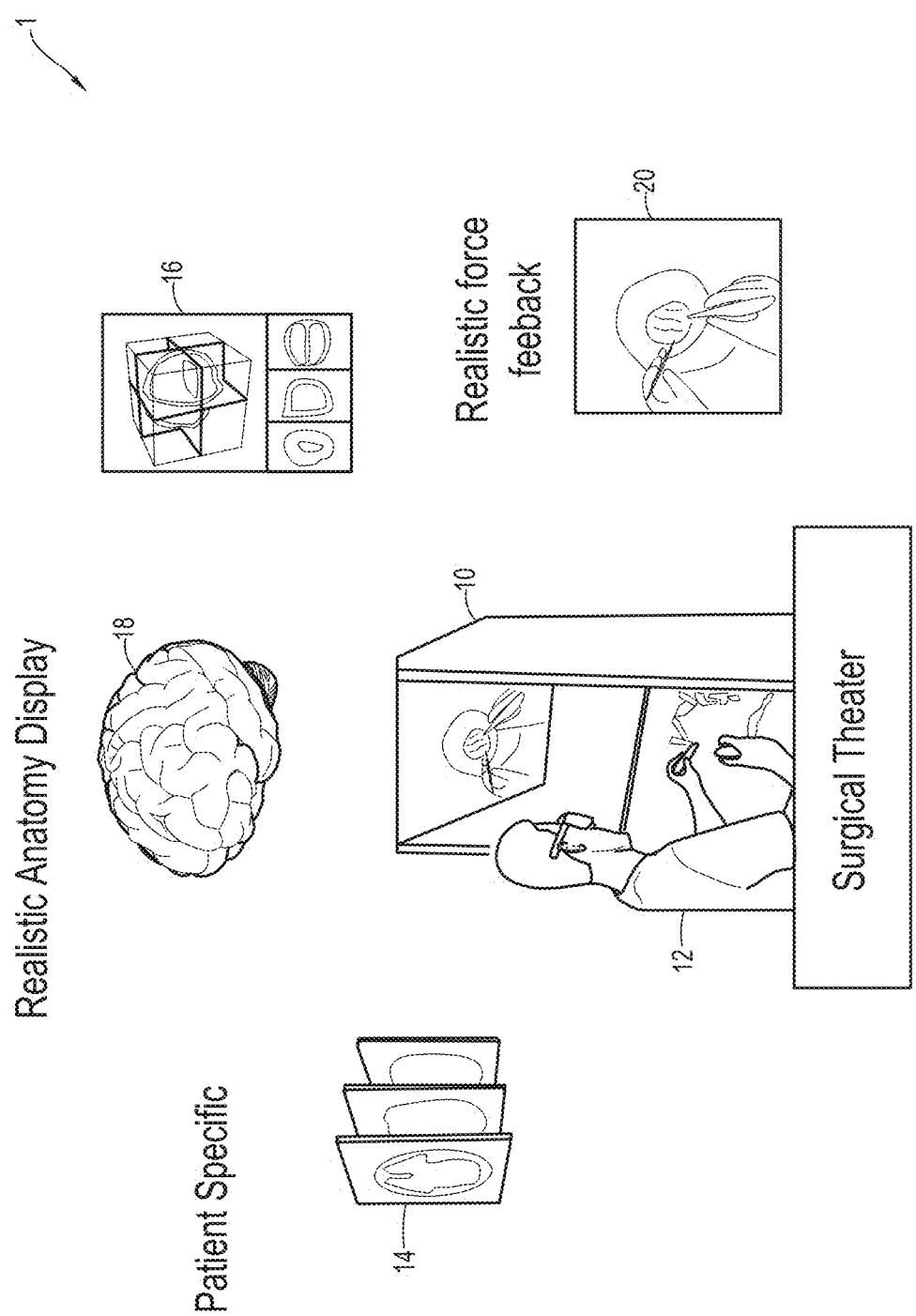
FIG. 1 provides a high-level schematic of an example Surgical Theater system.

FIG. 1 provides an example embodiment for one application of the system 1 where a patient specific scan image (CT, MRI or similar) (14) is fed to the system's console (10), an algorithm that creates a 3 dimensional realistic anatomy display (18) adds texture, shadow, shadowing and other cues to the image, a mechanical properties algorithm (16) assigns mechanical behavior characteristics to the image and transfer the image from static/still image to a dynamic and interactive image/model. Interfaces with or without force feedback (20) are connected to the system allowing the surgeon/operator (12) to manipulate the image/model that the system creates; the surgeon can select tools and implants from libraries of tools and implants including characteristics of those tools and implants. The surgeon then performs a virtual surgery on a manipulateable, dynamic and interactive 3 dimensional image/model of his patient organism in a realistic and dynamic manner.

The system includes an executive program that runs and manages all the system components and updates the status of the sub components according to the surgeon/operator (12) actions. For example, when the surgeon uses the interface (20) to push a tissue (such as by using a chose tool) that he sees in the display (18), the mechanical properties model (16) receives the information regarding the force that was applied, e.g., the direction of force; the tool that is being used including its material and shape and other mechanical characteristics of the tool, then the mechanical properties are used to calculate a new state of the 3 dimensional orientation an ad setup of the image according the force that was applied, the executive program send the calculated 3 dimensional matrix to the realistic anatomy display (18) that was created by the mechanical properties algorithm (16), the realistic anatomy display calculates the new image and its cues due to the change of image e.g., a new set of shadows and shadowing due to the new orientation of the image components are determined. Simultaneously, the mechanical properties model (16) send a set of parameters to the force feedback interface (20), these parameters include information of the force that the surgeon/operator (12) needs to sense due to the interaction with the organs (the force that the organ returns after the surgeon pushes or otherwise interacts with the tissues). This process of calculation of new stage at each one of the system's components (14, 16, 18, 20) is executed rapidly and continuously in cyclic manner, and each cycle is completed within a frame time of milliseconds, allowing the surgeon/operator to receive real-time and realistic cues and real-time reactions to his actions.

Figure 1A:
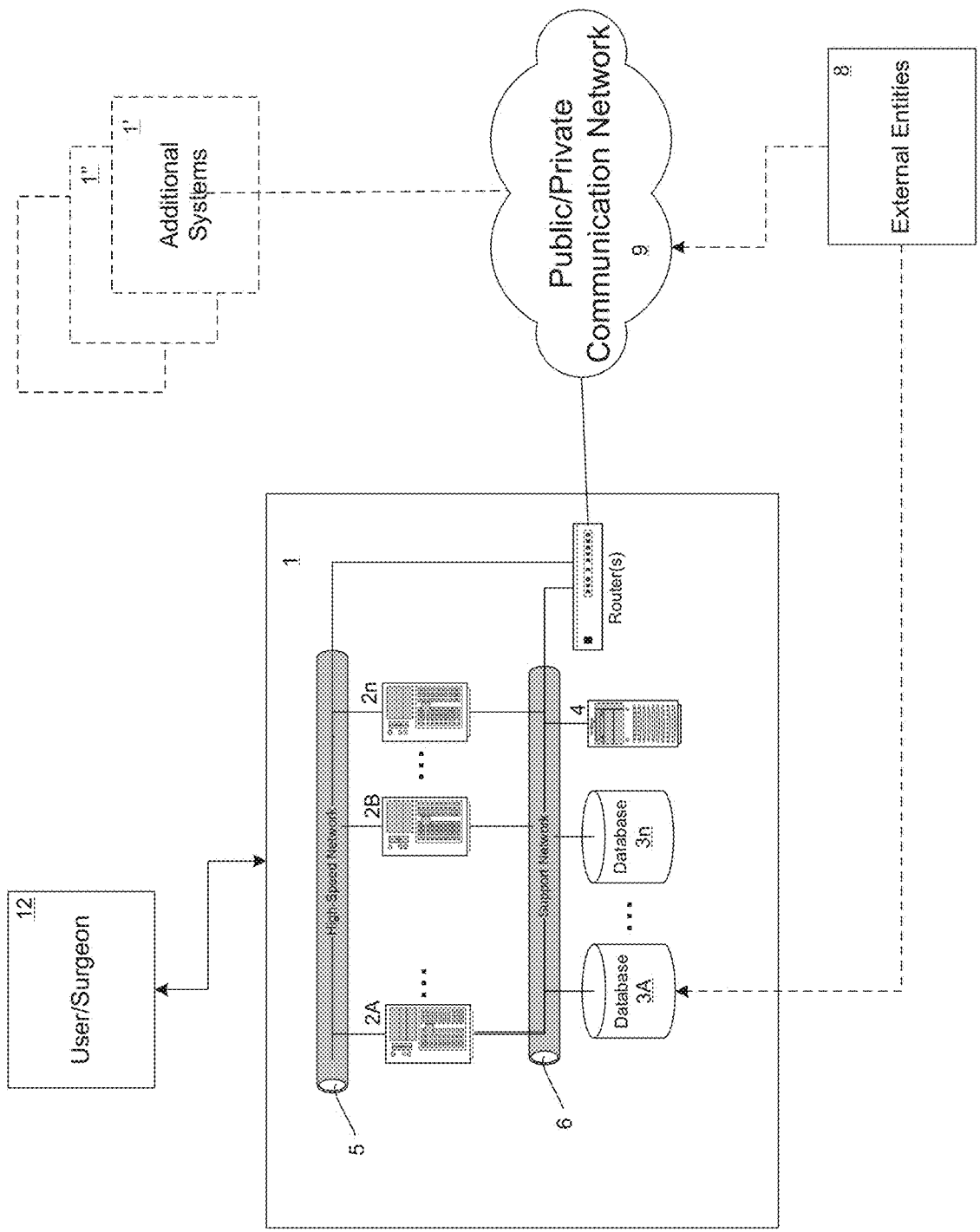
FIG. 1A provides an example computer system structure for implementing an example Surgical Theater System.

The Surgical Theater is a system, as shown in FIG. 1A, that integrates one or more computers (PCs) 2A-2n, one or more databases 3A-3n and other hardware components (e.g., networks 5, 6) and proprietary software into one complete system 1 (see both FIGS. 1 and 1A) that is structured into an immersive chamber/console sized about as big as a small walk in closet (see console 10 in FIG. 1). Once the surgeon 12 starts the system, the surgeon loads the set-up parameters of his patients which include details of the patient to allow the system to up-load the relevant data, the Surgical Theater than loads all the patient's available CT and MRI images from a patient images 14 into the database(s) 3 and other information that concern the simulated models such as patient age, gender, and so on (some or all of which may be obtained from external entities 8, such as medical databases, for example). The system utilizes tissue information parameters 16 from a system database. The system 1 performs a segmentation process and identified the Entities of the organ, Entities are vessels, tissue, tumor, and so on to create the simulated image model 18 shown to the surgeon on the display of the device. The system provides realistic tactical feedback 20 via feedback mechanisms to add further realism to the simulation.

The system applies the layers of the realistic visual, the mechanical properties and other relevant parameters 16 from the system database(s) and characteristics relevant to the case, all applied on the top of the CT and MRI images 14 from the patient images database(s) 3 and synchronized with those images. The synchronization creates, for example, vessel mechanical properties that are 'clamped' or 'attached' to the vessel images and so on to provide realistic simulation capability. The surgeon can be provided the ability to "fine tune" the models and adjust the mechanical properties of a certain area of the organ. For example, the surgeon may adjust the elasticity and other mechanical characteristics of the Entities behavior.

Subsequently, after such a set-up, the Surgical Theater projects the 3 dimensional organ model 18 presented in a realistic visual fidelity with realistic features such as; texture, shadowing and other features that adds realism to the simulated image. Each segment of the visual model 18 is coordinated and corresponds with an appropriate mechanical properties model from the system database 16 and other relevant properties of the specific case.

At this stage, the system allows the surgeon to browse and chooses from the system's virtual libraries 16 in the system database the relevant surgery tools and other elements (in the system software terms those tools and elements are "Entities" as well) that he may need to perform the surgery (or other procedure). Such elements may include; seizers and clamps, clips for aneurysm, artificial heart valves, and other elements appropriate for the specific case. (Adding additional systems 1', 1" . . . connected to the system 1 via a network 9—such as over the Internet or a private network—can result in a collaborative theater platform, described in more detail later in this disclosure.)

All of the various Entities are represented by the system in high-fidelity distributed models and functioning in a distributed architecture, e.g., each Entity typically has a separate subEntity, where the subEntity is, for example, a "visual entity" or "mechanical entity" and so on. Each subEntity exists in one of the different environments (e.g., the visual system environment, the mechanical modeling environment and so on, described in more detail below) distributed among a plurality of computers. Each such subEntity is responsible for its own performance (e.g., presenting the realistic visual of the Entity, or performing the Entity's mechanical operation).

The subEntities communicate via a distributed network (described in more detail below) to synchronize and coordinate the subEntities into a one integrated Entity compound model. For example, when a tissue is being pressed by a surgery tool, the surgery tool pressure characteristics (e.g., the location, orientation and amount of pressure and so on) is distributed via the network, each one of the subEntities is responsible for 'listening' and concluding if it is being affected by this surgery toll pressure; once a subEntity determines that it is being affected, each such subEntity (for example, tissue Entity) models the affect on their subEntity model, e.g., the visual subEntity, presents the visual effects (such as bloodiness of the tissue), and the mechanical properties models the shift of the tissue. Each subEntity distributes the change—for example, the tissue location and dimension changes—over the network so the other subEntities will be able to determine if they are being affected by this change. At the end of such action, all the subEntities of the tissue for the above example, (and the other Entities), become accustomed to, and, if needed, adapt their states and the models to, the new action that was sourced and initiated, in the above example, by the surgery tool.

Thus, the various functions (subEntities) can be distributed among various computers connected in a peer-to-peer network utilizing distributed data and state duplication (for keeping local copies of the state of the simulation), all listening on the network for any action that impacts their portion of the simulation, in which case they update their parameters via the network to keep the system accurate, which may, of course, impact other functions in other subEntities, which will therefore catch that fact by their monitoring of the network, leading to further updates, and so on. In this way, the system distributes the functionality among many computers in a parallel fashion so that updating can occur much quicker than it could if only a single computer were used. Only those subEntities impacted by a change need respond, and thus network traffic can be reduced to essentials.

The Surgical Theater allows the surgeon to record his actions and save them for later playback, to demonstrate his surgery plan to the chief surgeon or resident, or, to share information with other surgeons, demonstrate new techniques he is working on, practice the surgery, and so on. The system's interfaces to the surgeon includes surgery interfaces (e.g., seizers handles) that include force feedback that is delivered to those tools to allow the surgeon to sense the force feedback cue of his actions, realistically simulating an actual procedure.

Once the surgery tools and the other Entities are selected by the surgeon, they are integrated into the virtual surgery scene and turn into an integrated element of the simulated scenario including realistic visuals features and mechanical properties and operation properties features that are applied to each one of those selected items. For example, the simulated scissors reflect mechanical characteristics of real scissors and will cut in the simulation as the real scissors do, and, aneurysm clips, when placed at the simulated vessel, simulates blocking the blood flow.

Next, the surgeon performs the surgery actions at any stage of the virtual surgery; the surgeon can "freeze" the simulation and rotate the organ to observe the area of his interest from different orientations and perspectives. The surgeon can "mark point of time" of the virtual surgery and can command a "return to the mark point". For example, the surgeon can mark the time before clamping an aneurysm and return to this point of time while "un-doing" all the actions that took place after this point of time. In this fashion, the surgeon can evaluate different surgery approaches of a selected phase of the surgery without restarting the entire surgery from the original starting point. Several such 'mark points' are available allowing the surgeon to return and "re-do" actions and exams/rehearse on several selected phases of the surgery. Surgical Theater use may include surgeon rehearsals toward a surgery; surgeon demonstration to the chief surgeon or resident; surgical practice and development, testing, and validation of tools and methods, and knowledge sharing. Hands-free operation, as described below, can be utilized for this feature.

Collaborative Theater

Figure 2:
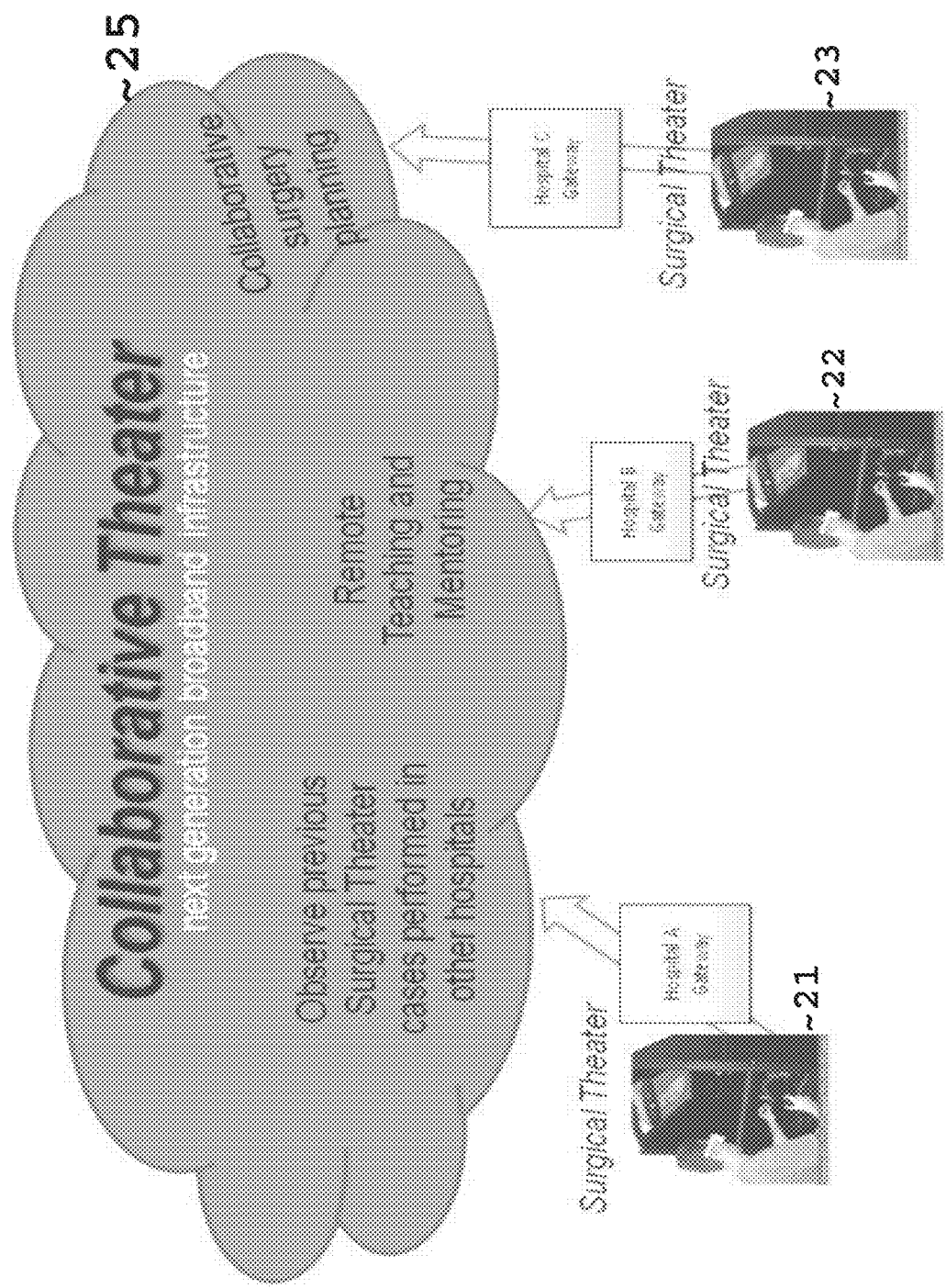
FIG. 2 a high-level diagram of an example of the Collaborative Theater concept using a plurality of the Surgical Theaters networked together.

FIG. 2 shows a high-level example implementation of the Collaborative Theater concept that was introduced with the Surgical Theater. By leveraging next generation broadband infrastructure 25, individuals using SRPs 21, 22, 23 ... from different hospitals will be connected allowing surgeons across the nation and across the globe to collaboratively plan a surgery case, e.g., surgeons from two or more distributed sites step into their SRP and rehearse, together, on a patient case toward a surgery. This Collaborative Theater allows surgeons to study the best practice methods by observing previous Surgical Theater cases as well as providing remote teaching and mentoring. The Collaborative Theater allows all the hospitals that are connected and using the SRP to gain access to the up to date accrued knowledge and most recent "best practices". Again, hands-free operation, as described below, can be used for the collaborative theater concept.

System Level Design

The system level design description is outlined in the preceding sections. The visual rendering engines analyze 3D MRI and CT patient-specific images and create computerized segmented modules that represents the anatomical structures and features of the particular image. The medical market has a vast number of advanced Digital Imaging and Communication in Medicine-DICOM (1) viewers. Their feature sets range from layered black and white slices in 3 different panels that could be cross-referenced to a complete ability to fly through static subsets of 3D images of patient's organs. In addition, there are 4D and 5D features that record various functional and dynamic changes of organs in a form of a movie clip. As magnificent as those captured images or moving sequences might be, they are a fixed set of snapshots images in time.

The Surgical Theater takes existing 3D conversion processes and adds the features specific to the human tissues and structures based on physical and mechanical properties that are then stored in the system database. Once this patient-based model is set in motion in the virtual world, the Surgical Theater introduces a set of virtual surgical tools that allow the surgeon to manipulate (push, cut, clamp, etc.) those models similar to real surgery tissue manipulation, providing an intuitive experience for the surgeon.

Figure 3:
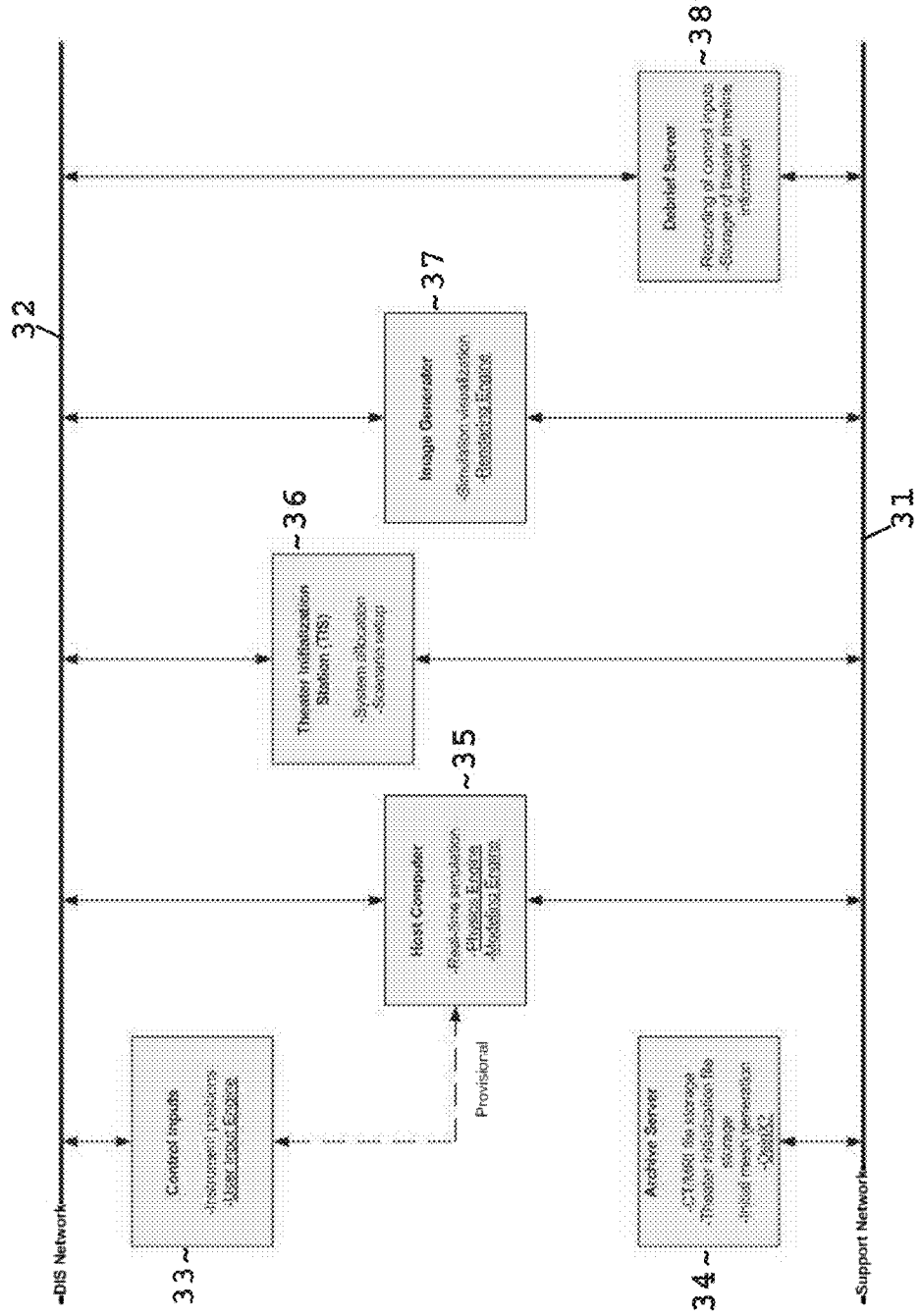
FIG. 3 shows an example breakdown of a distributed simulation network concept for example Surgical Theater embodiments.

FIG. 3 provides a breakdown of an example Surgical Theater distributed simulation network (Surgical Theater DIS (ST-DIS) is presented). Each of the components (i.e., blocks) in the figure is an isolated computation station (that can be executed on a stand-alone computer or collection of computers) with a designated set of functions. The stations are appropriately connected with a regular support network 31 (such as an Ethernet network, for example) that handles slow irregular traffic, like transferring of vast amounts of DICOM data. Upon more intense data processing demand, the stations are supported by a specialized Distributed Interactive Simulation (ST-DIS) Network 32 that is a hardware isolated network used only for high priority simulation data (which can be implemented in high-bandwidth Ethernet, for example). The ST-DIS Network 32 carries volatile simulation information and allows for such an exquisite simulation load distribution.

The Surgical Theater's ST-DIS is a network architecture for building large-scale virtual worlds from a set of independent simulator nodes. The simulator nodes 33-38 are linked by the networks and communicate via a common network protocol (such as TCP/IP, for example). The ST-DIS infrastructure enables various simulators to interoperate in a time and space coherent environment. In the Surgical Theater's ST-DIS system, the virtual world is modeled as a set of "Entities" that interact with each other by means of events that they cause. The simulator nodes 33-38 each independently simulate the activities of one or more of the Entities in the virtual world of the simulation and report their attributes and actions of interest to other simulator nodes via messages on the network. The other simulator nodes on the network are responsible for "listening" to the network messages, determining which ones are of interest to them (based on the Entities they are simulating) and responding appropriately.

One of the features of the ST-DIS network and simulation architecture concerning distributed interactive simulation is that there need be no central server or processor. Each simulation application maintains its own copy of a common virtual environment in its own memory or database. Representations of this environment are distributed by various means to all simulation applications prior to any real time operation. ST-DIS is basically a peer-to-peer architecture, in which data is transmitted available to all simulators where it can be rejected or accepted depending on the receivers' needs. By eliminating a central server through which all messages pass, ST-DIS reduces the time lag for a simulator to send important information to another simulator. This time lag, known as latency, can seriously reduce the realism, and therefore the effectiveness, of a networked simulator. Effective distributed simulation depends on very low latency between the time that a new state/event occurs for a simulated entity to the time that the state/event is perceived by another entity that must react to it. Any delay introduced by the training device could result in negative reinforcement to the trainee.

Referring again to FIG. 3, the Archive Server 34 is generally used to perform the tasks of downloading and retaining in a database large amounts of data necessary for simulation. In addition, the Archive Server 34 can be used to prepare obtained data for further use in the simulation. Note that because its duties are typically global in nature, and not critical to the simulation activity, the Archive Server 34 is typically only connected to the support network 31.

FIG. 3 shows a network architecture that includes an off line "support" network (31) that "Archive Server" (34) that loads the medical images (CT/MRI) and additional initialization data stored in a database (for example, the patient name, age and so on and files to be included in the scenarios such as surgery tools libraries) "Debrief Server" (38) that records control inputs and store the scenarios and all the actions in a timeline information and allows playback of scenarios and actions. The real time network (32) is the network that transfers messages between the systems node during the simulation in a real time fusion—one way for implementing this network can be a Distributed Interactive Simulation (DIS) network (32), the components that connected to this network are; Control Input (33) that connected to the surgeon/operator systems interfaces, this node has an optional direct physical connection to the Host Computer (35) that may be implemented in a case that the real time requirements of the system cannot be satisfied by the DSI network and a direct physical connection between those node sis needed. The Host Computer (35) includes the executive manger program and other models and simulation components and it is responsible for the real time synchronization and timing of the entire systems.

The Theaters Initialization Systems (TIS) (36) performs that system allocation and setup for each one of the nodes, for example, when the surgeon select a specific tool to use, the TIS allocates/activates the appropriate models of this tool for generating an accurate tool simulation (with tool characteristics stored in a database) for all the nodes assuring that all the nodes are set up with the same initialization. The Image Generator (36) performs the rendering and visualization tasks of the scenarios. The Host Computer (35), the TIS (36), the Image Generator (36) and the Debrief Server receive and exchange information with off line for initialization from the Support network (31) and receive and exchange information with the real time network (32) for "on line" and real time simulation.

Needed organ surface and volume data are extracted from an existing MRI/CT scan stored in the database. To obtain 3D organ surface data, the system can use a DICOM viewer and data management system such as the OsiriX (or comparable) that is open source software implemented for Apple Macintosh computers, for example. By "tapping into" OsiriX's ability to generate 3D surfaces of organs and organ groups based on the voxel density values with Objective C source code, the Surgical Theater adds an ability to store information about the 3D surfaces and organ types that describe into a flat file in a database. The entire set of parts of this study stored in this manner in the system database so that it is later transferred to the Image Generator Station 37 that recreates the patient-specific images based on standard characteristics of the organs. Once the necessary rendering data is obtained, the rendering platform for Image Generator Station 37 is applied to the image. For this, a proprietary Image Generator algorithm is integrated (such as a Flight IG; see the features in the separate headings for the Realistic Image Generator—RIG) with a Visualization Tool Kit.

The IG has unique features that deliver fine cues such as shadowing, texture, and material properties that are assigned to the visual models and as further detailed in the RIG sections. Not only does the IG create realistic and fully immersed environments by using those features, it can also process large volume of visual data base models under hard real time constraints. Enabled by the combination of the DIS architecture and the "Entity" design, the network traffic is minimized and the anatomy of the peer-to-peer nodes create a highly efficient real time system.

After the patient-specific images have been successfully rendered, various physics libraries are added in order to create proper simulation. Pushing and manipulation of the brain tissue is simulated using extensive research embodied in modeling platforms such as the OpenTissue (or comparable) collections of libraries that are available. The OpenTissue, for example, is an open source collection of libraries that models volumetric shells and other complex behavior of 3-dimensional shapes. Customized libraries can also be developed for use. Specificity of the brain tissue physics and mechanics properties that derived from the research of mechanical properties of brain tissue in tension can be utilized, for example. Experimental papers are available that provide mathematical models of the mechanical manipulation of animal brain samples. Dynamic and realistic interaction of simulated surgical tools with the simulated tissues are implemented in the algorithms and approaches as described in co-pending patent application PCT/US12/31514 filed on Mar. 30, 2012, and U.S. Pat. No. 8,311,791 filed on Oct. 19, 2010 (incorporated herein by reference). The work looks at various tools and tissue types to create a realistic simulation specifically for implementation of surgical simulations.

The software code of the example Surgical Theater is written in a commercial environment such as C++, with the code being designed to run in windows operating system, a Linux system, or compatible. In the coding development process, emphasis is given for the code real time execution and code efficiency all aimed to maintain a real time system performance while minimizing the latencies.

The visual system driver located in the Image Generator (37) is designed with an optimizers environment, such as OpenGL or similar, enables high-performance rendering and interaction with large models while maintaining the high model fidelity demanded, providing attention to detail while maintaining high performance in a cross-platform environment.

For computing efficiency purposes, each of the visual model's Entities have several Level of Details (LOD) representations; high LOD is presented in areas of the simulation scene in which the surgeon needs high resolution at, and, lower LOD is presented in areas of the simulation scene in which the surgeon has no immediate interest or interaction with. For example, tissue visual model is presented in high LOD in the area around the surgeon interaction and with lower LOD in areas that the surgeon doesn't have immediate interaction with. The LOD can be dynamically adapted: a surgeon's actions such as pointing the surgery instruments toward a specific area can be utilized by the LOD optimization algorithm for the dynamic allocation of the LOD for specific section of the visual models.

The typical system's computer is a PC with a multiple core (multiple processors) which provides flexibility and growth potential. The computer system includes random access memory, Ethernet ports, system disk, and data disk.

For the validation of the Surgical Theater (image quality, realism, image controller and manipulation), the skills and experience of senior surgeons are utilized. The surgeons are used to evaluate the system by performing specific surgical procedure while comparing it against their vast neurosurgical experience as well as against a specific case that they have already operated and is being simulated in the Surgical Theater.

Figure 4:
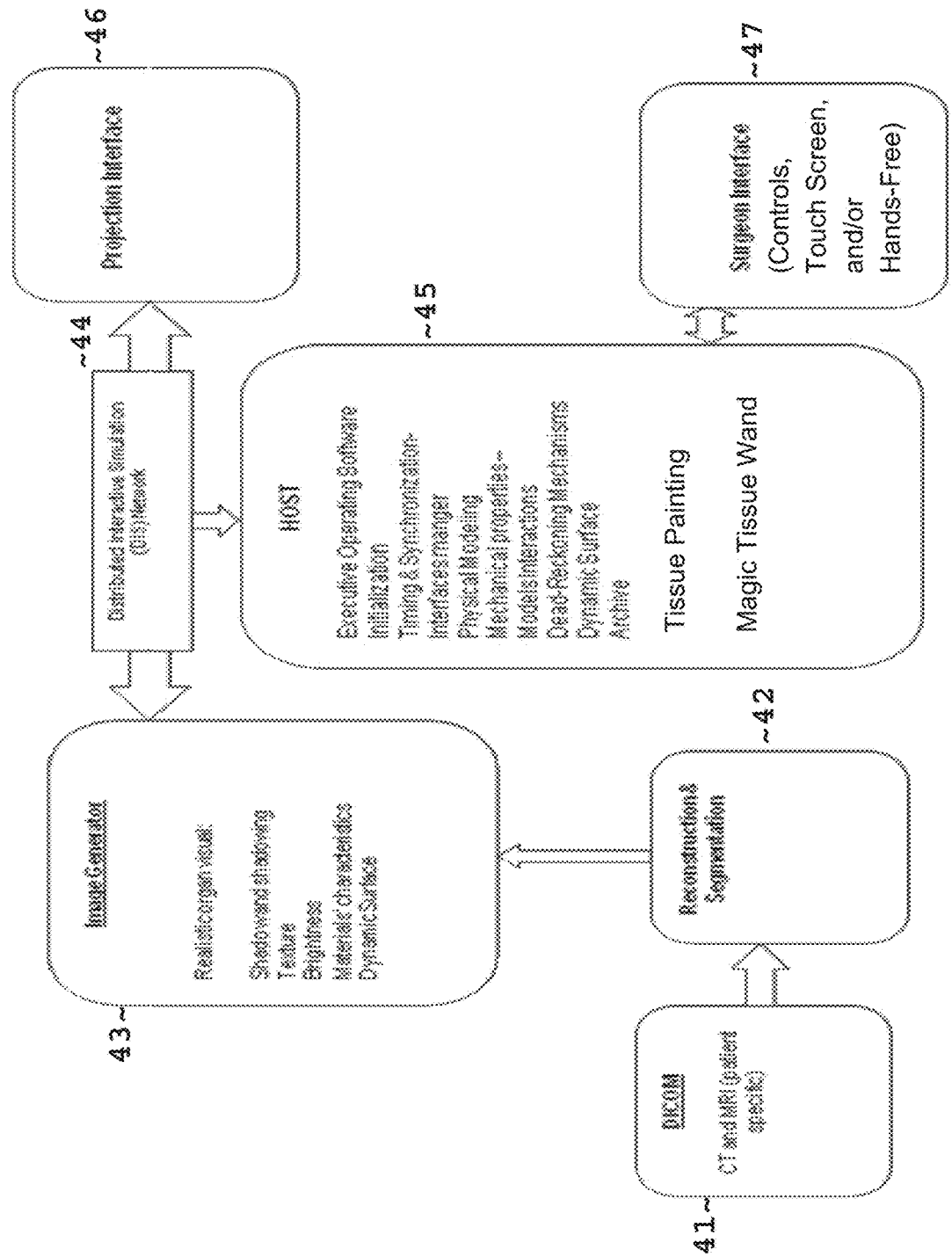
FIG. 4 is a block diagram showing example software functionality for an example Surgical Theater system.

The Surgical Theater Block Diagram of FIG. 4 describes the functionality and the flow of the process (vs. the actual network connection of FIG. 3) from the row data of the scanted image DICOM 41 through the process of segmenting the row data (to identify soft tissue, vessels and so on). Then the Image Generator assign visual representation of each segment (shadow texture and so on), this image is connected via the DIA 44 network to a projection interface 46 and to the Host 45 that will update the image generator 43 with the surgeon actions that are connected through the Surgeon Interface 47 and the mechanical Properties and other modeling that the Host includes that all will reflect the new state that the Host will send to the IG 43 during each simulation cycle.

By eliminating the central server through which all messages pass, ST-DIS dramatically reduces the time lag for one simulator (computer) to send important information to another simulator (computer). This time lag, known as latency, can, if too large, seriously reduce the realism, and therefore the effectiveness, of a networked simulator. Effective distributed simulation depends on very low latency between the times a new state/event occurs for a simulated entity to the time the state/event is perceived by another entity that must react to it. Any delay introduced by the training device results in the negative reinforcement to the operator (e.g., the surgeon).

According to the recommended practice for communications architecture (IEEE 1278.2), the underlying communications structure should support 100 ms or less latency for packet exchange for closely coupled interactions between simulated entities in real-time (e.g. simulating high performance aircraft in a dogfight or simulating a surgeon performing brain surgery). This requirement is based on human reaction times that have been the basis of Human-In-The-Loop (HITL) flight simulator designs for many years.

Within the ST-DIS system, the virtual world is modeled as a set of Entities (as described previously) that interact with each other by means of events that they cause. An Entity is a sub-component in the simulated scenario, such as tissue, specific characteristics (such as—tissue mechanical properties,) creating a sub group of that "tissue entity". Another Entity can be a blood vessel, for example, and so on. Each Entity can have several subEntities that operate in a distributed manner (such as on different simulators/computers). Together, those subEntities are combined to create the complete Entity model. Those subEntities are, for example: the Visual subEntity that holds and simulates the Entity's visual feature and characteristics, or, the Mechanical Properties subEntity that holds and simulates the Entity's mechanical feature and characteristics. Each of those sub-Entities model code can run in a different computer (or group of computers) such as a PC, and they communicate with each other as well as with other Entities via the ST-DIS network. The simulator nodes, independently simulate the activities of one or more Entities (or subEntities) in the virtual world of the simulation and report their attributes and actions of interest to other simulator nodes via messages on the ST-DIS network. The other simulator nodes on the network are responsible for "listening" to the network messages, determining which ones are of interest to them (based on the entities they are simulating) and responding appropriately.

The above-described Surgical Theater architecture is based on this Distributed Simulation concept thereby enabling pioneer and exclusive abilities to deliver a premier fidelity which is an essential requirement for creating immersive scenarios crucial for the rehearsing of open/classic surgeries where the surgeon(s) interacts with the organ(s) by direct human sense. As each Entity is divided to its sub-components (visual, mechanical properties and so on), and as each of those subcomponents/Entities' simulation code runs in a separate computer, this can maximize the computation power, and by that the creation of a unique and exclusive premier fidelity, fine cues, and computing capabilities while handling terabytes of information under hard "real-time" constraints while maintaining real time performance (e.g., less than 100 millisecond latency), the core capability of the Flight Simulation technology.

The Surgical Theater facilitated a visual rendering engine which analyzes 3D MRI and CT patient-specific images and creates computerized segmented modules that represents anatomical structures and features of the particular image. Medical market has a vast number of advanced DICOM viewers, but as magnificent as those captured images or moving sequences might be, they are based on a fixed set of snapshots in time. The Surgical Theater takes existing 3D model conversion algorithms and adds the features specific of the human tissues and strictures based on physical and mechanical properties creating a "living" image with models that reforms the patient specific CT/MRI images according to actions taken by the surgeon and based on the models that simulate the mechanical properties of each pixels in the image and realistic visual characteristics models. Once this patient-based model is set in motion in the virtual world, a set of virtual surgical tools (that can include aneurysm clips and clip appliers, implants such as bone joint implants, or other devices) are introduced allowing the surgeon to manipulate (push, cut and etc.) those models similar to a real surgery tissue manipulation. Thus, the Surgical Theater provides an intuitive experience for the user.

For the Image Generator, the Surgical Theater of the example embodiment integrates a proprietary Flight Simulation Image Generator algorithm with a visualization code such as Visualization Tool Kit (VTK). As detailed in the following sections, the Surgical Theater Realistic Image Generator has features that deliver fine cues such as shadowing, texture, and material properties that are assigned to the visual models.

The Realistic Visual Sub System

This section focuses on the "realistic visual" segment of the Surgical Theater that is a modification of a Flight Simulation Image Generator that is capable of rendering satellite images into realistic 3 dimensional images and models that are converted into the Surgical Theater realistic Image Generator (MG) handling and real time rendering CT/MRI DICOM images into a patients' specific realistic and dynamic CT/MRI images and models that are crucial for the open/classic surgeries where the surgeons interact with the organ by direct human sense.

The use of a visual system in the creation of the immersive simulation system in the field of Human factor Engineering is important; studies demonstrate that a high percentage of the immersion is constructed and contributed by the level of fidelity and realism of the visual system that the operator (e.g., pilot or surgeon) interacts with. Findings show that operators who rehearse on high fidelity visual systems completed the memory task including self-report of confidence and awareness states in significantly higher levels than the low fidelity group. A significant positive correlation between correct 'remember' and 'know' responses, and in confidence scores, are found when utilizing high fidelity, realistic simulation.

As outlined above, the Surgical Theater creates a realistic "life-like" digital rendition of the surgical site and the surrounding tissues/structures. Since this digital rendition is patient-specific and "life-like", it sets Surgical Theater apart from other simulators that use generic imagery to create approximate renditions of the surgical site, or, other system that simulates noninvasive procedures such as endoscopic, vascular and similar procedures, where the surgeon/operator interfaces the organism with a camera that has its own visual characteristics that are defined and limited by the camera specification and are very different from the visual characteristics of the bare and direct eyes view of the open/classic surgeon's where the surgeon interacts with the organism with direct sense of his eyes However, realistic "life-like" rendering presents a surmountable task due to the complexity of the properties of the living biological tissues. In order to create such high degree of realism, the Surgical Theater includes a Real Image Generator add-on (RIG): a visual system where patient-specific images of the surgical site, together with surrounding tissues, is realistically presented and can be manipulated in this all-purpose manner.

Figure 5:
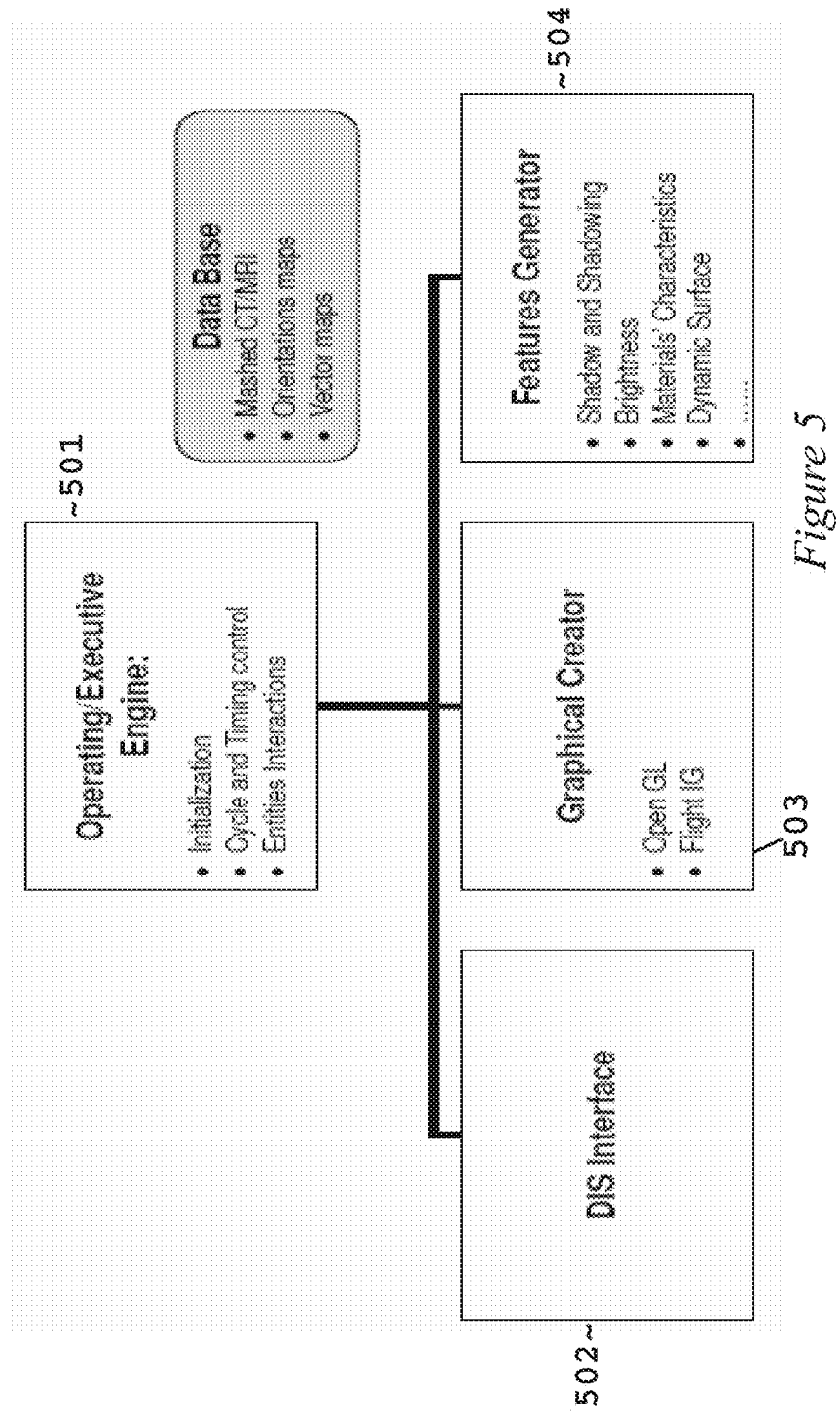
FIG. 5 is a diagram showing high-level Realistic Image Generator (RIG) platform.

FIG. 5 shows a RIG Architecture Block Diagram. Data Base box—collection of the mesh modules based on the patient-specific CT/MRI, 3D and segmented images, pre-processing of the images, smoothing, masking, scaling. Graphic Creator box—Interface to the graphics card. ST-DIS Interface box—Interface to the ST-DIS network. The figure shows a hierarchy diagram of the visual systems. The system includes an executive program that runs and manages all the system components and updates the statutes of the sub components according to the surgeon/operator and the status of all the sub components as they are read through the DIS network (502). The Operating/Executive Engine (501) is responsible for the initialization of all the software and hardware components in a way that all the system's components are working with the same data bases (for example, the set of tolls that the surgeon choose). When the scenario starts, the Operating/Executive Engine (502) performs the cycle and timing control and perform the task of managing each component to complete its calculation cycle within the time frame that it is planned on in a way that all the system's sub components receive the information from the other sub components on a timely manner allowing the overall system to complete the simulation cycle in a given time frame. For example, when an action is taken by the surgeon and transmitted by the DIS network (502), the Feature Generator (504) reads the relevant part of this action/consequence of this action as calculated by the mechanical properties algorithm, the Graphic Creator (503) change the image according to this action (for example, move a vessels that was pushed by the surgeon), then calculates the changes that need to be applied on the image as a result of this change, for example, creating a shadow resulted by the change of the vessel location and orientation. This cycle is executed rapidly and continuously managed by the Operating/Executive Engine (501) in a cyclic manner in a way that each cycle is completed within a frame time of milliseconds allowing the surgeon/operator to receive real time and realistic cues.

Figure 6:
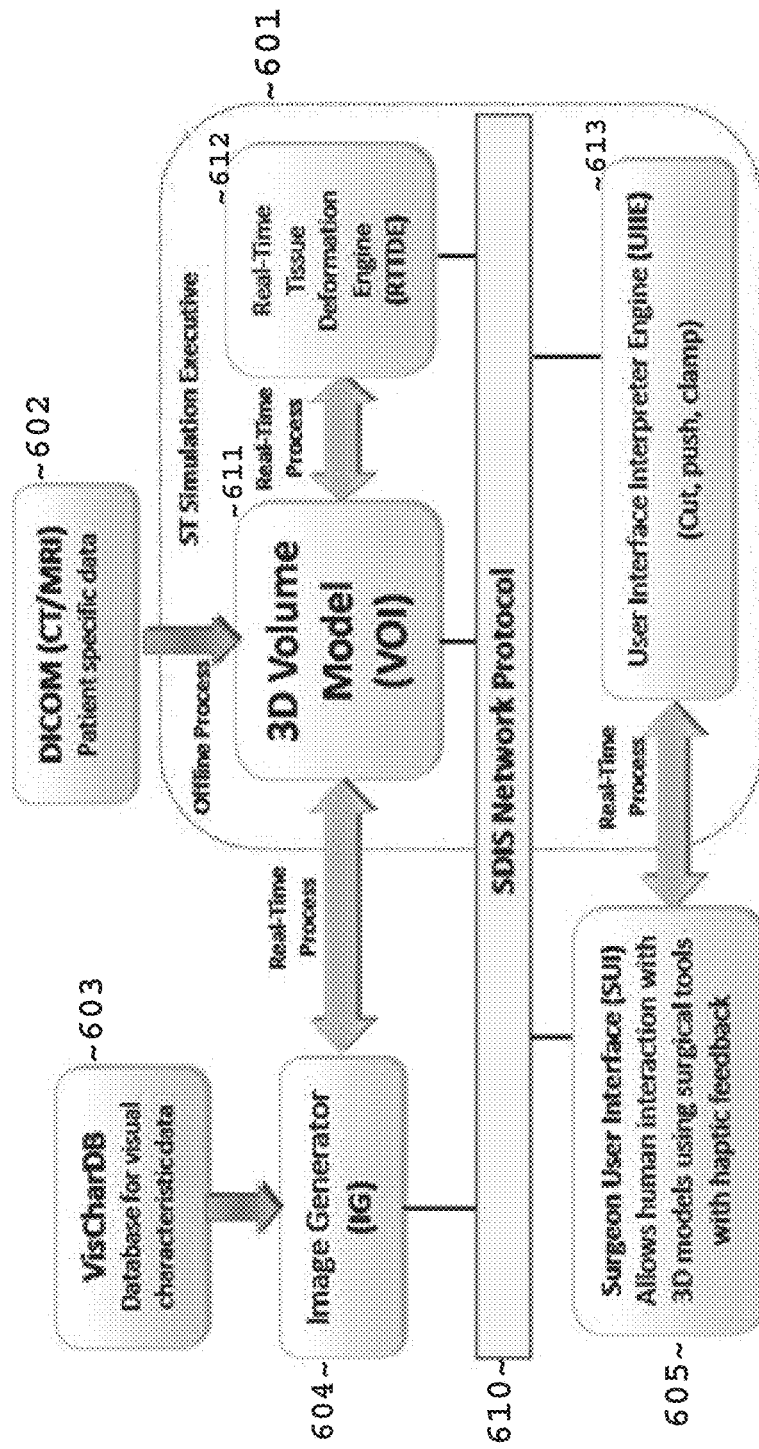
FIG. 6 provides an example high-level architecture and workflow of a Surgery Rehearsal Platform (SRP) for an example Surgical Theater system.

SRP General Description:

The SRP creates realistic "life-like" full immersion experience for the neurosurgeon to plan and physically rehearse cerebral aneurysm clipping surgery by converting patient-specific DICOM data of the surgical site and surrounding tissues/structures into a dynamic and interactive 3D model. Unlike existing surgery preparation devices, the SRP can provide: (i) fine cues of look, feel and mechanical behavior of patient-specific tissues, (ii) 3D display of the patient-specific anatomy, (iii) real-time, surgery-like manipulation of 3D tissue model and, in the future, (iv) haptic feedback to the surgeon for a "full immersion" experience. Due to the complexity of organization and mechanical properties of living biological tissues, developing such a realistic "life-like" rendition will require following sub-developments (FIG. 6): (i) DICOM Image Volume Reader (602) and Viewer with built-in segmented Volume of Interest (VOI) Model Generator (611), (ii) 3D Image Generator (IG) (604), (iii) Real Time Soft Tissue Deformation Engine (RTTDE) (612), (iv) Surgical Distributed Interactive Simulation (SDIS) Network (610) (v) Simulation Executive Application (SimExec) software (601) (vi) Surgeon User Interface (SUI) (605), and (vii) User Interface Interpreter Engine (UIIE) (613) (vi) VisChasDB database for the visual such as tools library heartbeat, blood flow and others (603).

The conversion of a set of 2D patient-specific DICOM data into a segmented 3D VOI Model with accurate patient-specific tissue attributes is done using DICOM Volume Viewer (611) (proprietary software developed by Surgical Theater LLC). First, patient-specific DICOM data set undergoes image enhancement stage using mathematical algorithms adapted for a 3D dataset (603). This enhancement stage will increase image smoothness and reduce image noise without affecting the ability to distinguish between different tissue types.

Next, using a multi-panel view window within the DICOM Volume Viewer (602), the surgeon defines VOI, i.e. surgical site containing aneurysm and surrounding vessels and structures. The next step is tissue segmentation, i.e. initial tissue-specific intensity ranges are assigned to tissues using Top View window of DICOM Volume Viewer to yield 3D VOI Model with high-resolution, quality, customizable data structure, and tissue-specific segmentation. The 3D VOI model is stored in a patient-specific repository and accessed during the cycle of operation as follows: (I) 3D Image Generator (IG) (604) presents the surgeon with high-fidelity visual representation of the model via graphical interface; (II) the surgeon manipulates the model using realistic surgical tools inside the Surgical User Interface (SUI) (605); (III) User Interface Interpreter Engine (UIIE) (613) translates surgeon's manipulations into a set of mathematical values that together with other patient-specific inputs (e.g. heartbeat, blood flow and others) are applied to the model by the Real Time Tissue Deformation Engine (RTTDE) (612). As the model changes, the IG (604) reflects those changes to the surgeon in real-time, thus completing one simulation cycle. Smooth, continuous, "life like" SRP flow is achieved by repeating cycle ≥60 times per second by the IG and 20 times per second by the RTTDE (612).

SDIS Based Architecture:

The SDIS based architecture facilitates a unique and exclusive ability for premier fidelity, fine cues and computing capabilities while handling large volume of information under hard real-time constraints while maintaining real time performance which is the core capability of the Flight Simulation technology. One of the features of the SDIS network is that there is no central server or processor, each simulation node (nodes may be: Image Generator, User Interface, Mechanical Modeling computer and so on) maintains its own copy of the common virtual environment—vessels, tissues and other models that are held and maintained at each of the simulation node; each such model is handles as a separate "Entity". This architecture enables several PCs to work together in a synchronized manner under hard real time constraints allowing SRP's pioneering and unique capabilities to deliver a premier fidelity of the simulated scene. This creates an immersive scenario that allows rehearsal of open/classic surgeries where the surgeons interact with the organ by direct human sense.

Once the surgery tools and the other Entities are selected by the surgeon, they are integrated into the virtual surgery scene and turn into an integrated element of the simulated scenario including realistic visuals features and mechanical properties and operation properties features that are applied to each one of those selected items, for example—the scissors have the real mechanical characteristics and will cut as the real scissors do, and, Aneurysm clips, when placed at the vessel, blocks the blood flow.

Figure 7:
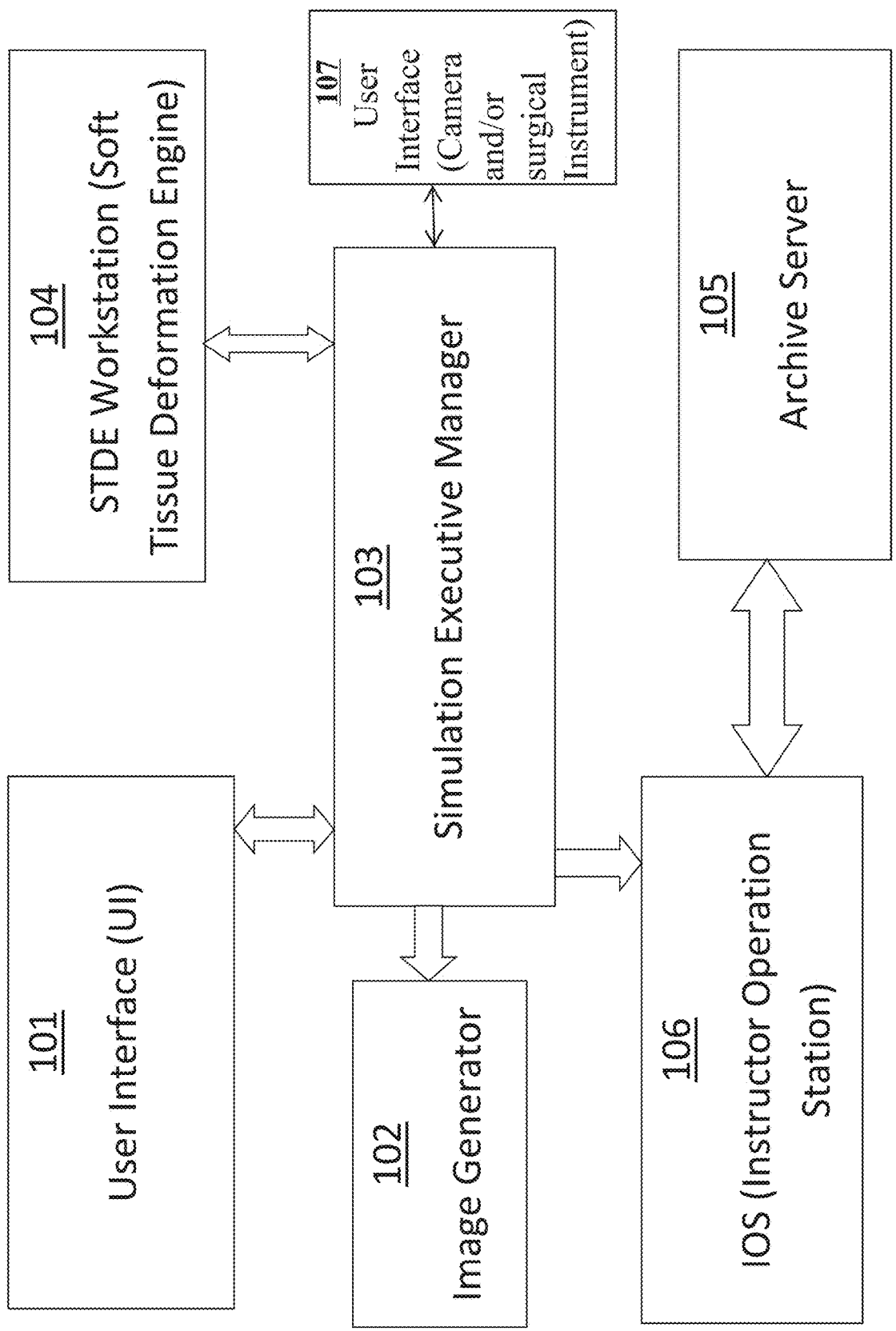
FIG. 7 provides an example computer architecture for the example SRP.

The SRP system as is compose by the following units or combination of sub parts of the units depended on the configuration, volume that needs to be simulated and the specific application. These are similar to those for the Surgical Theater system as shown in FIG. 4, but modified as described in this section. The sup components can run in Several separated Computing Processor Units in multiple PCs (FIG. 7).

The workstation that the surgeon works on is the User Interface 101. The Image Generator 102 operates similarly to the like device in the Surgical Theater. The Simulation Executive Manager 103—synchronizes the real time operation of the system, runs, and executes the modeling programs. The STDE Workstation 104—This PC handles the STDE (Soft Tissue Deformation Engine). The Archive Server 105—This station holds all the relevant files and data and able to record the procedure for future debriefing and data collection, and this PC also serves as the network domain controller. The IOS (Instructor Operation Station) 106 is for monitoring and controlling the training session, also allowing the instructor to "inject" events. Also serve as the "Master of Ceremony" and will activate the whole training session. One or more User Interface 107 is provided for hand-free control and/or for tracking real surgical instruments, as described below.

Each of these Computing Processor Units connects via the SDIS network with a network switch (not shown).

Surgical Interface

Figure 8:
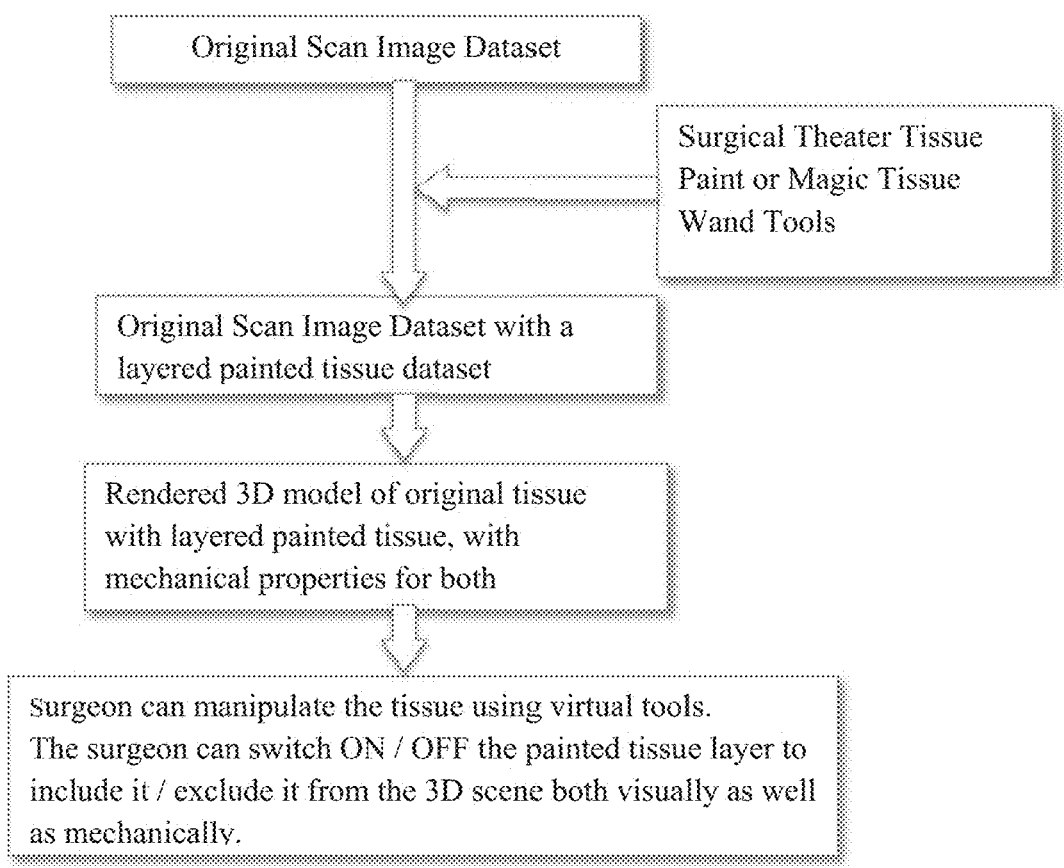
FIG. 8 is a flow chart showing example tools for adjust the dynamic tissue images.

As discussed above and in the related applications, the updated Surgical Theater provides a method for a hybrid rendering (volume and surface) of images from a scene file (for example, a medical scan file) of multiple formats (for example, a Digital Imaging and Communications in Medicine—DICOM) into an interactive image/scene. The output image/scene may be 2-dimensional or 3-dimensional and will contain geometry, viewpoint, texture, lighting, shadow and shading information and other elements of the description of the virtual scene. FIG. 8 shows a flow chart showing the updated features, with the specific details discussed hereinbelow.

The interactive image/scene is constructed from elements that are both volumetric rendered elements and surface rendered elements. Furthermore, each element, volume or surface, interacts with one or more elements that are volume (see 112 of the image shown in FIG. 9) and/or surface elements (see 111 of FIG. 9).

Interaction between elements includes, but is not limited to, physical interaction such as: a collision model implemented to represent the interaction between elements that results with movements and/or reshape of elements that replicate the actual physical movements of the element according to physical conditions, such as pressure, elements material (elasticity, stickiness etc.), and collision condition such as collision angels and elements orientation.

The rendering process equation accounts for all lighting shadow ad shadowing phenomena and produce a final output stream that incorporates all the visual elements.

Surgical theater rendering software solves the rendering equation in real time while reflecting the physical interaction between elements while maintaining the realistic look of output image/scene/model.

Figure 9:
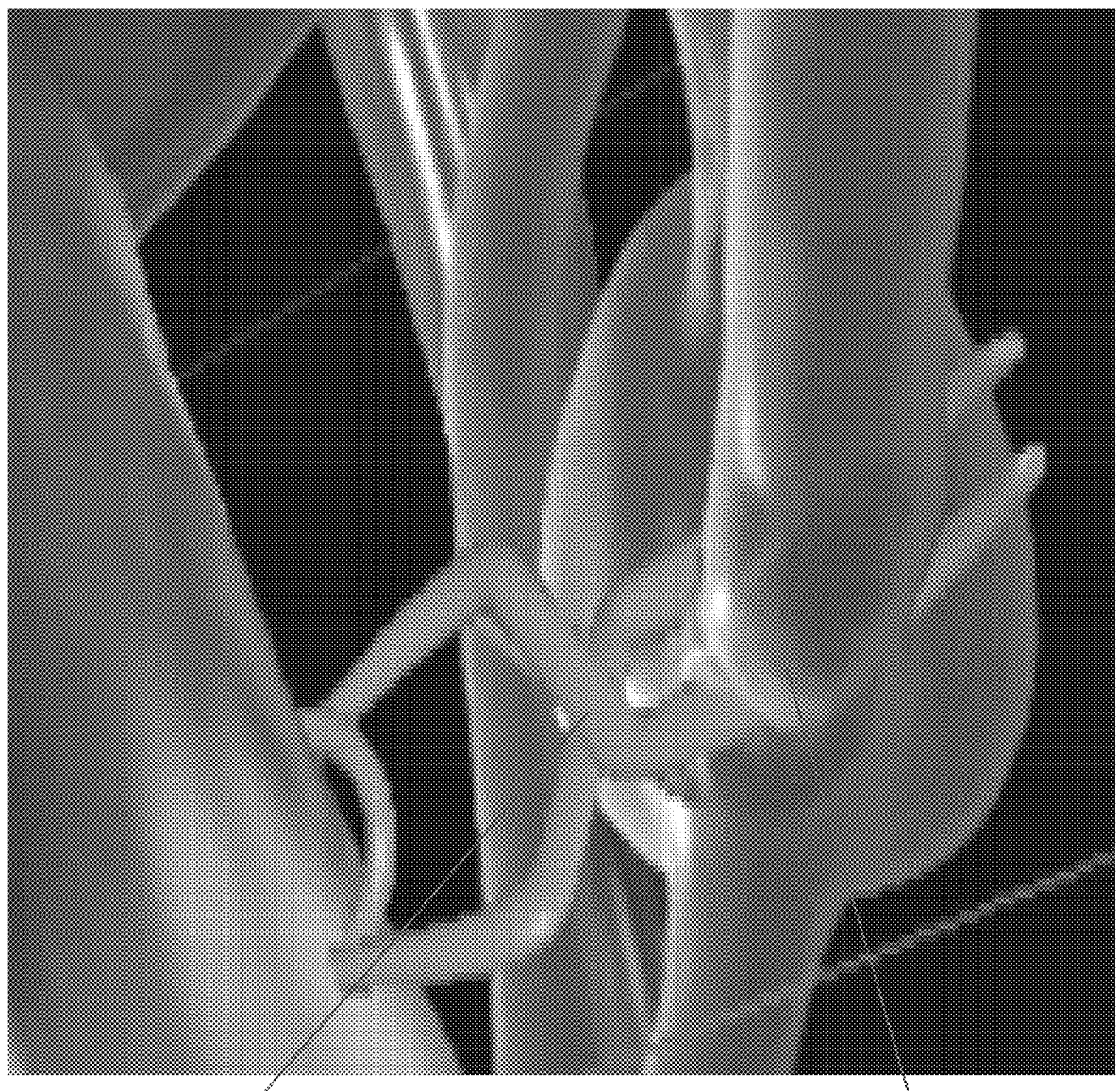
FIG. 9 is a screen shot showing example interactive tool and tissue elements.

For example, in FIG. 9 a clip 112 presses a blood vessel (volume rendered element) that results a reshape of the vessels 111. Users control the interaction control by either a mouse controller, a touch screen, 3D or 6D controllers, or by a hands free controller, described below.

Figure 10A:
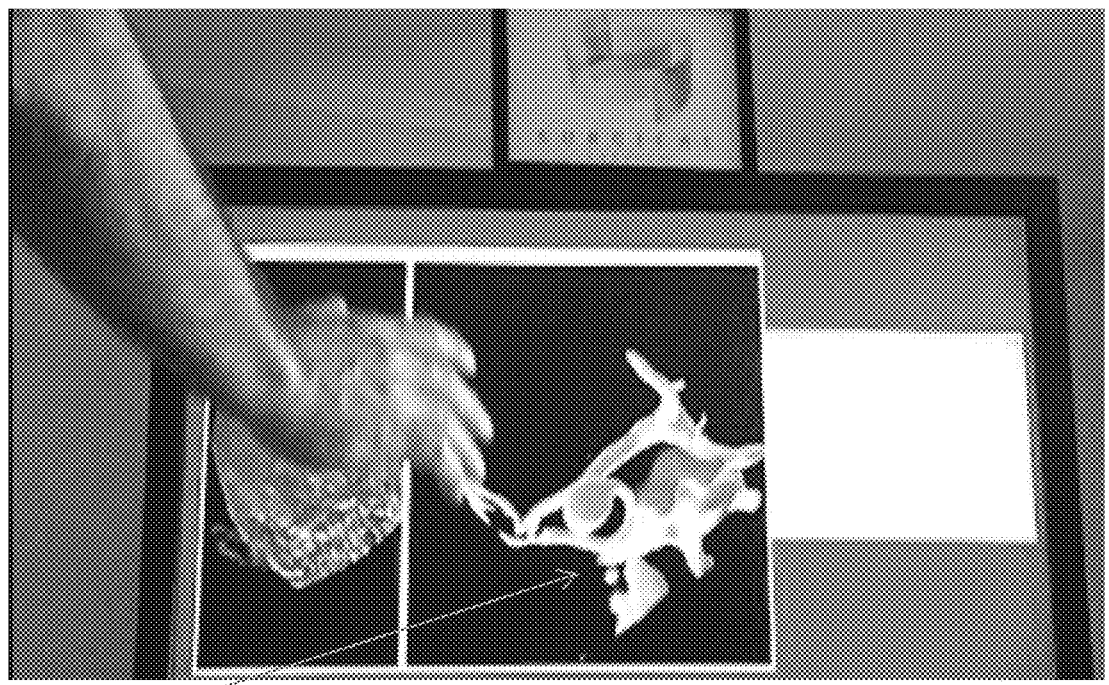
FIGS. 10A and 10B are images showing example hands-free input interactions.
Figure 10B:
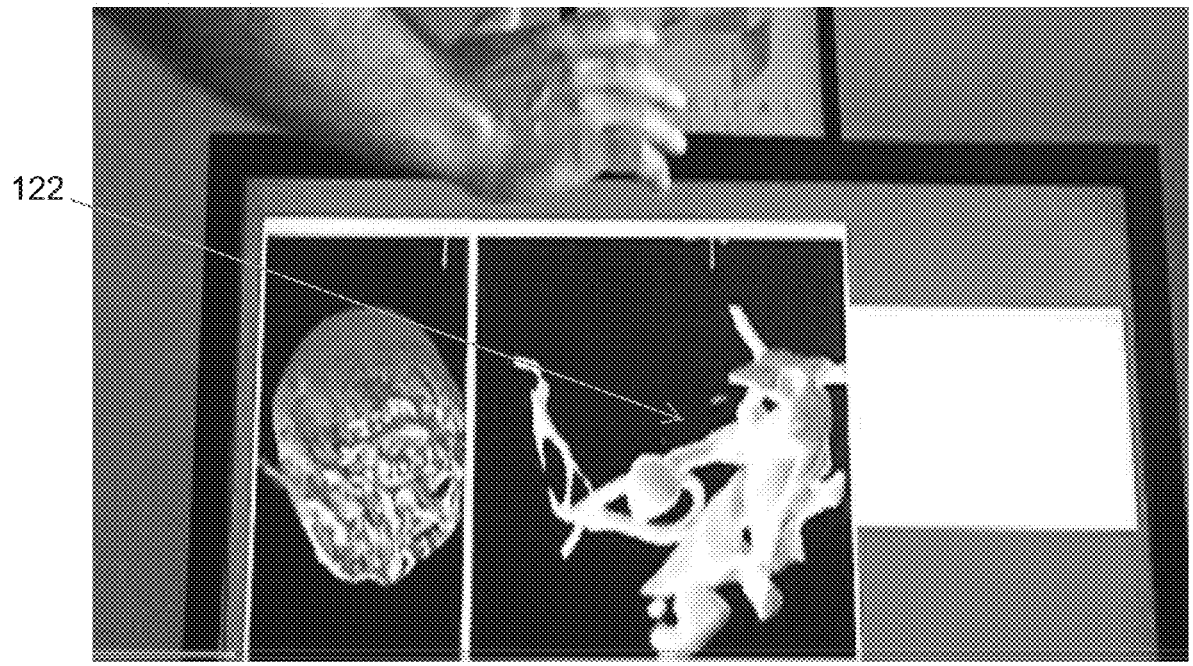

Hands free controller or touch screen: by integrating a camera-based device that captures and recognizes the users body's elements in real time (in a manner that may utilized technologies similar to the Kinect system by Microsoft, for example—see www.xbox.com/en-US/kinect/kinect-effect, with the Leap technology by Leap Motion being another example, see live.leapmotion.com/about.html both incorporated by reference, see item 107 of FIG. 7), or by a touch screen or any other interface, the user can interface and interact with the image/scene by waiving with his hands in a pre-defined ways, to control the image/scene (FIGS. 10A and 10B). The user can, among others, do the actions of:

Rotate, move, and shift the image/scene (see the hand motion shown in FIG. 10A to FIG. 10B, with the motion moving and re-orienting the image 121, 122, respectively)

Zoom in and out.

Select elements from a library and add them to the image/scene.

Drag and drop elements from in the image/scene.

Command one or more elements to interact with one or more other elements—for example, place a an aneurysm clip and command it to be closed on the aneurysm and then command "close" which causes the clip (surface element) to interact with the aneurysm (volume element) with the resulting physical squeezes of the aneurysm and the movement of the clip (form open blades to closed blades).

Select elements and remove them from the image/scene.

Scroll between slices if the image/scene is stacked/built from multiple slices (such as CT MRI)

Figure 11:
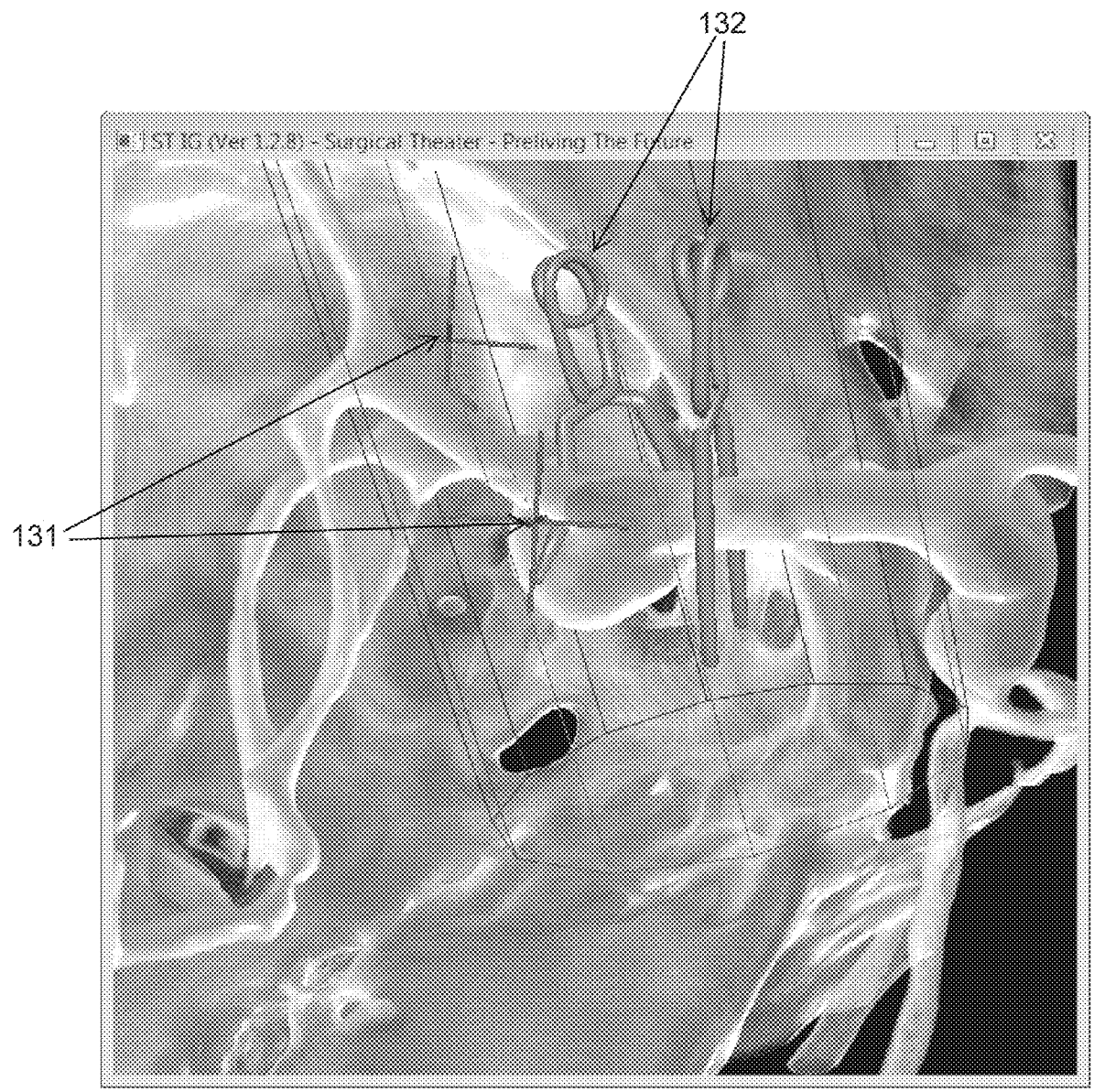
FIG. 11 is a screen shot showing an example marker and tools that can be dragged by a user.

Reposition objects in the scene by selecting them and then dragging them to the desired 3D position. This allows, but not limited to, cause tool to tissue interaction (in the case of a tool being dragged 132 in FIG. 11) or to perform measurements in the scene (in the case of dragging measurement markers 131 see FIG. 11).

"Painted Tissue":

General: medical images produced from scanner (such as MRI, CT and others) provide a physical, functional structural or other information about the scanned anatomical structure. Due to a variety of reasons, among others, the scanner limitation, not all the anatomical structures are clearly visible in the resulted image. Two examples for this phenomena/limitation are:

1—In MR scan nerves may not always be visible. Specific example may be in images of brain cerebral scans toward treatment of microvascular compression where a cerebral vessel touches a nerve and creates a physical pressures on the nerve—in those scans the vessel is often visible at the scanned image, yet, the nerve cannot be observed.

2—In MR, CT, or other scans, a part of anatomical structure may be visible, yet, due to verity reasons, among others, the scanner limitation, only part of the anatomical structures is visible. One example may be in images: in a CT or MRI scan, parts of the vessels structure may be visible while other parts are not. In this example, the vessel image will be distorted and/or not completed.

Figure 14A:
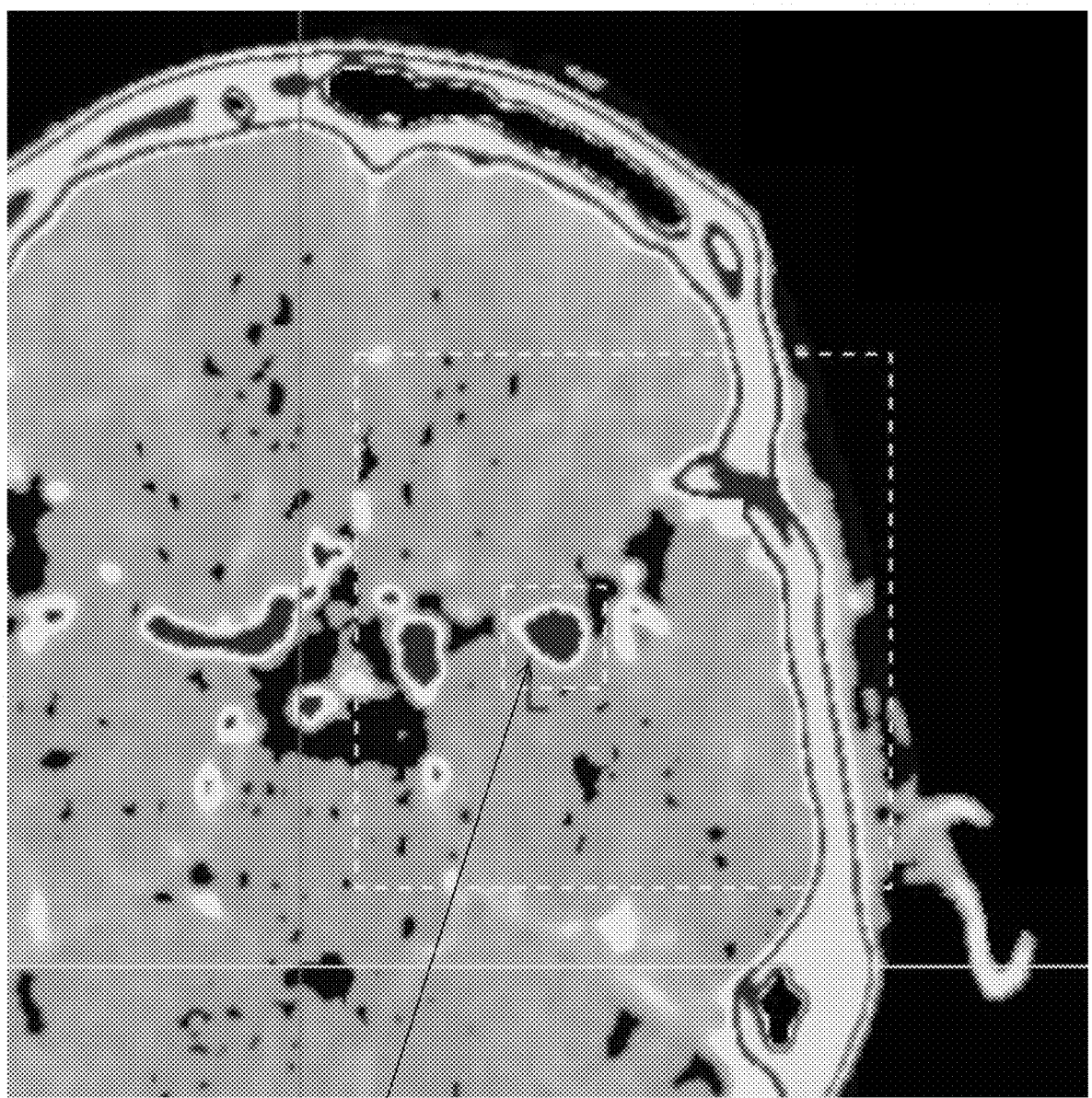
FIGS. 14A and 14B are screen shots showing example structures that can be modified using tissue painting tool.
Figure 14B:
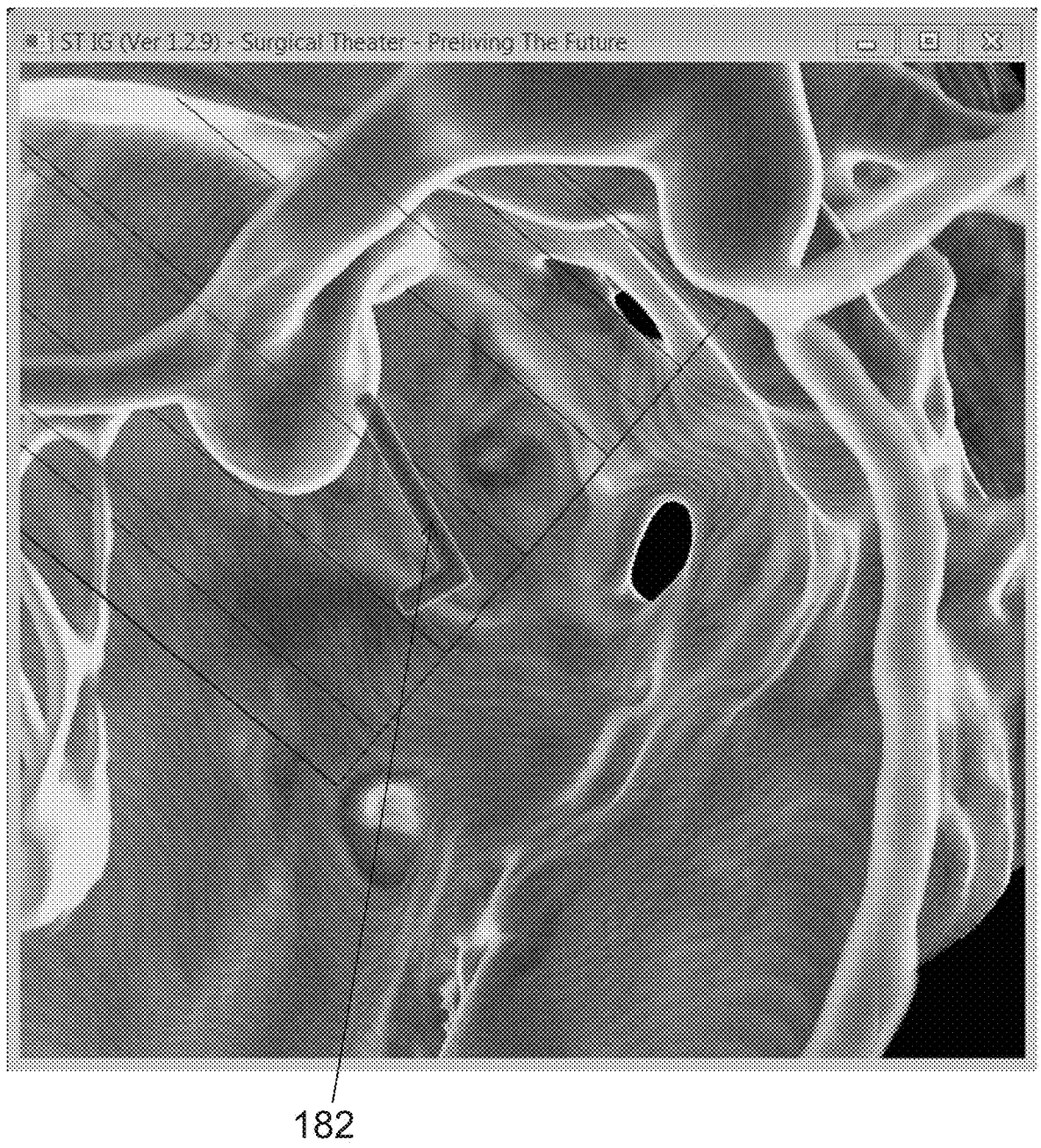

"Tissue Painting"—the developed algorithm and software tool provides the user an interface to draw any geometric shape or free hand drawing shape in 2- or 3-dimensions (e.g., line, circle, clinic, ball etc.). The resulted painting interface allows the user to determine the thickness of the line or the wall shell and walls of 3-dimensional shapes. The user can also determine the visual characteristics of the shape; the color, the transparency etc. The new shape is created in within the medical image in a way that allows the new created shape to become a part of the scan (Magic Tissue) and to be integrated with the scan image. For example, the user can draw a line that will represent a nerve. This nerve can be crated at a lengths, shape, color, transparency, location and orientation of the user selection. The user can place the shape in proximate to an existing anatomical structure observed in the scanned image (e.g., a visible part of the scan) and to "connect" it to an existing anatomical structure. The user also assigns this newly drawn shape to a specific tissue type. Once created, this new shape is rendered and added to the 3 dimensional anatomical model. The new shape can be rendered and reconstructed as a volume model or as a mash/polygon model. FIGS. 14A and 14B show examples of tissue painting at 181, 182, respectively.

"Magic Tissue Wand"—Due to a variety of reasons, including, among others, the scanner limitation, not all the anatomical structures are visible in the resulted image. Often an anatomical structure (e.g., a blood vessel) will appear only partially in an image and the entire structure will not be visualized; there will be missing parts of the anatomical structure and the anatomical structure will not be a whole continued/completed one. An algorithm and software tool is provided that completes the anatomical structure and reconstructs the image to create a more complete anatomical structure. The reconstruction algorithm utilizes analytical geometric calculations and calculations performed on the scanned image to analyses and to recreate the anatomical structure based on existing 'hints', cues and other signs in the scanned image in order to complete missing parts of the anatomical structure. This includes geometric and spherical distributions of similar voxel in the Hounsfield unit (HU) and the creation of vector of distribution to analyze and recreate the missing part of the anatomical structure (HU scale is a linear transformation of the original linear attenuation coefficient measurement into one in which the radiodensity of distilled water at standard pressure and temperature (STP) is defined as zero Hounsfield units (HU)—for example, the radiodensity of air at STP is defined as −1000 HU).

Figure 12A:
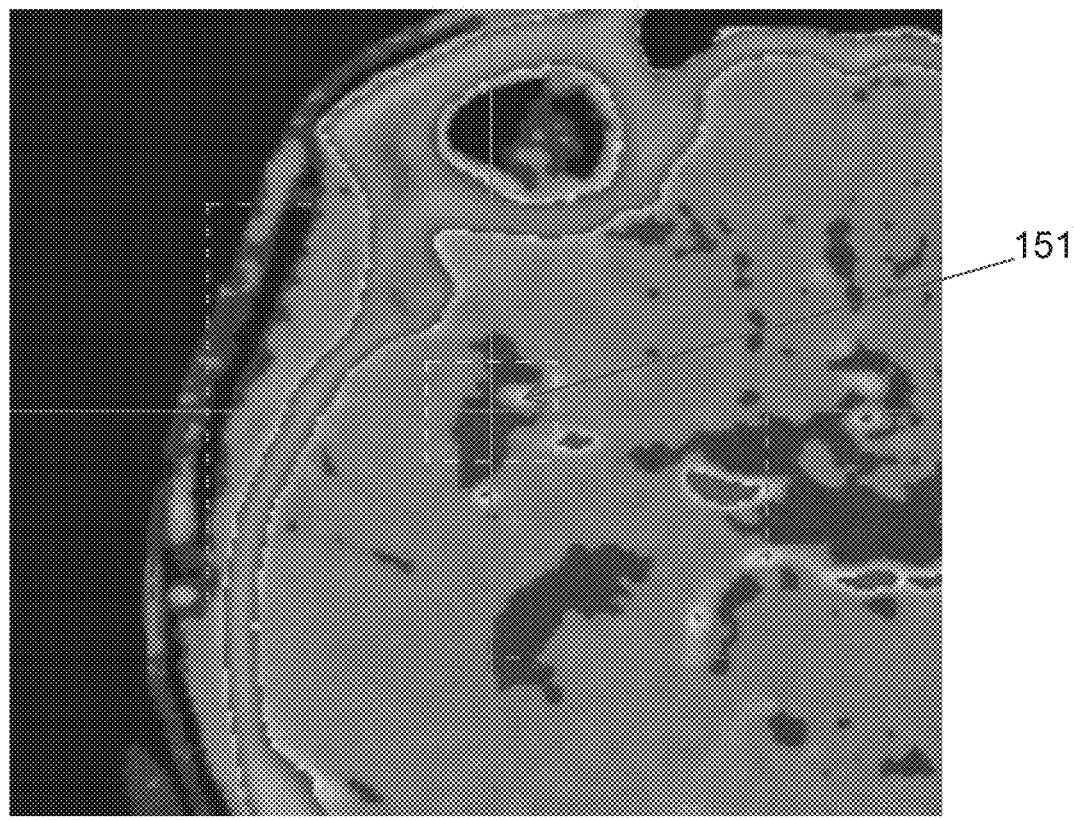
FIGS. 12A, 12B, 13A, and 13B are screen shots showing example structures that can be modified using a magic tissue wand tool.
Figure 12B:
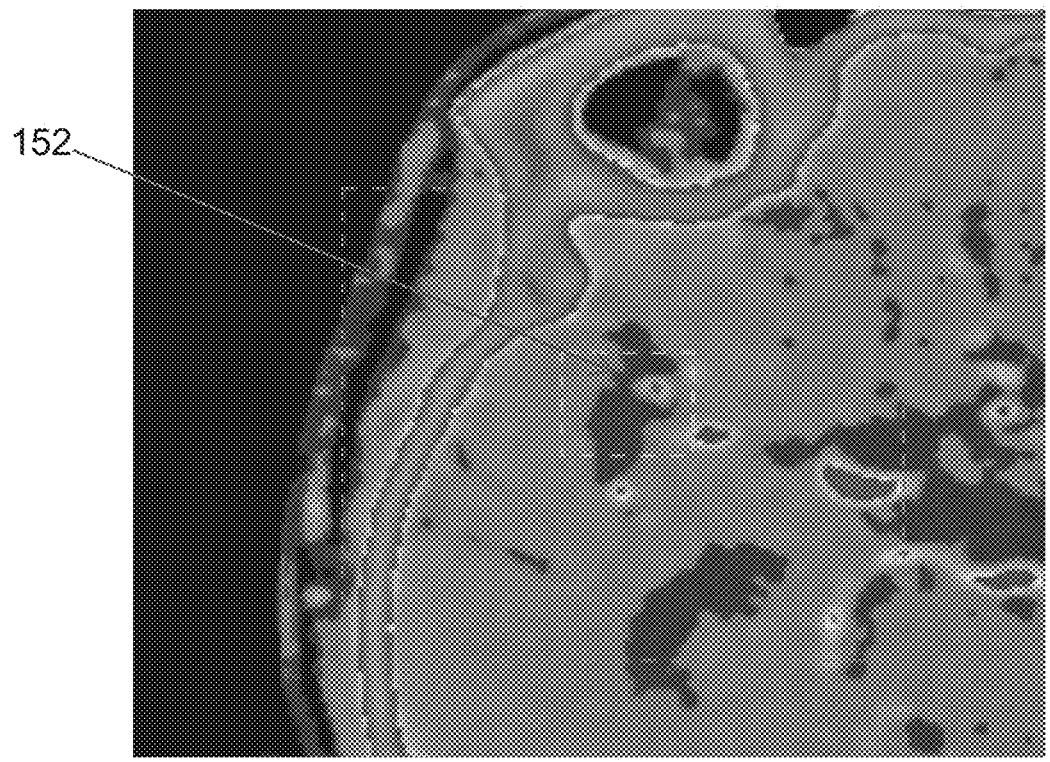
Figure 13A:
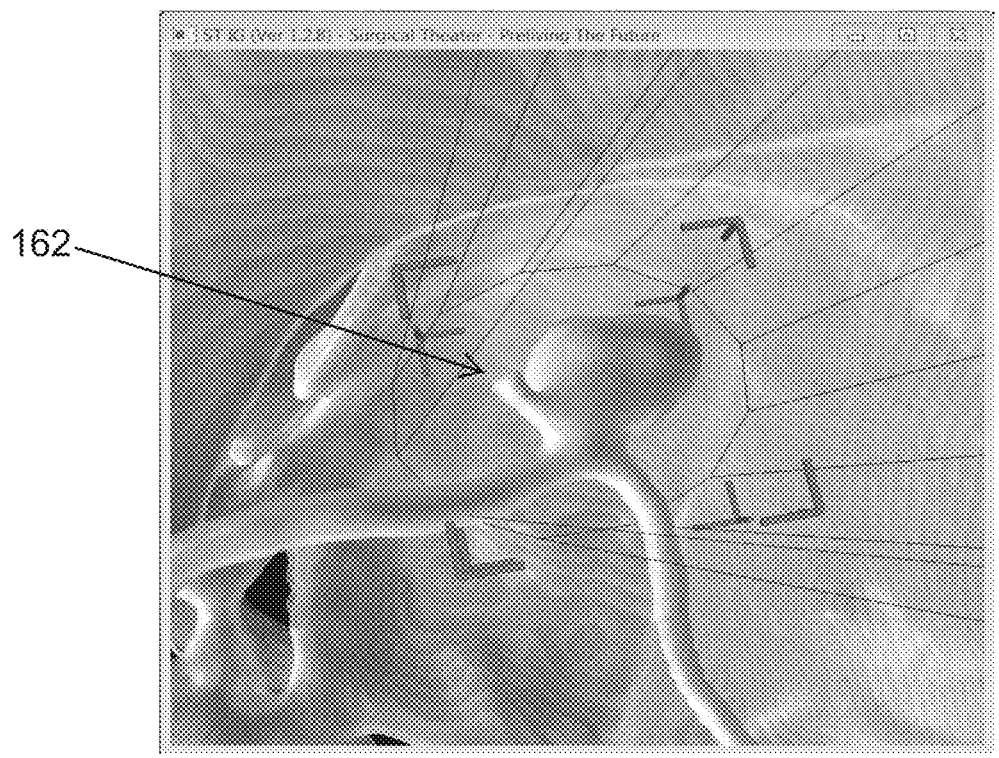
Figure 13B:
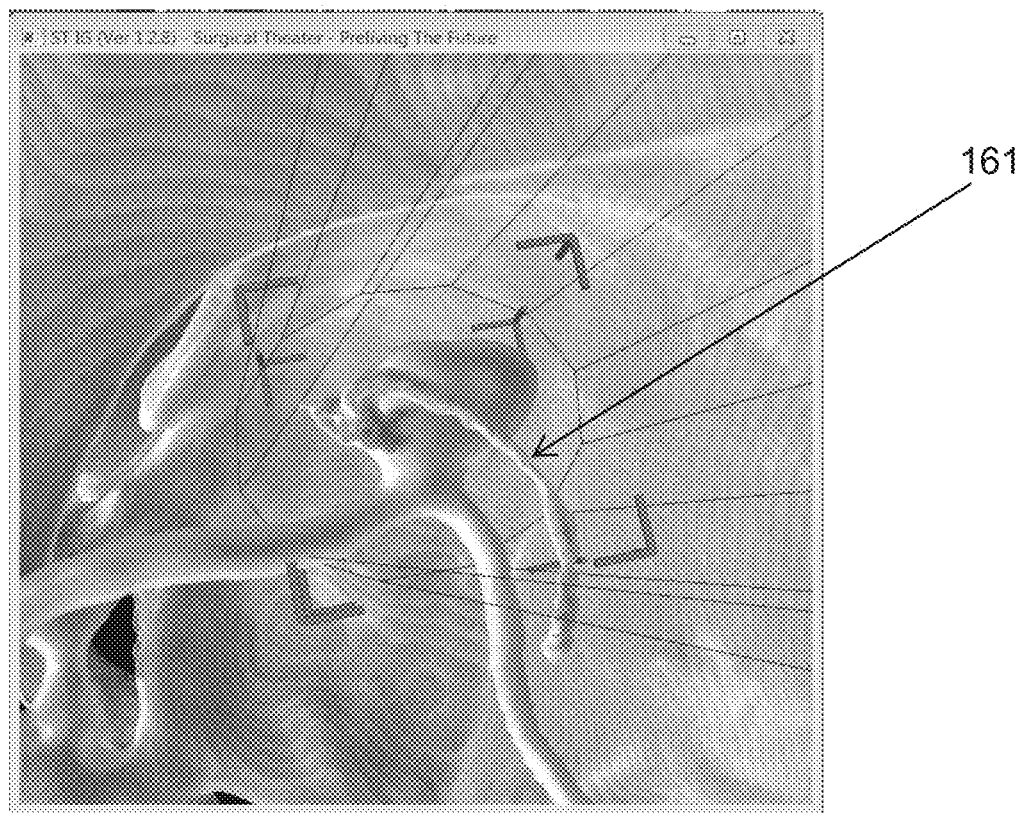

The Magic Tissue Wand algorithm connects the spherical distributions voxel in in a complimentary way—that is, voxel will be added to the original, incomplete anatomical structure (see item 152 of FIG. 12B and item 162 of FIG. 13A) if by adding those voxel together, the anatomical structure is more complete. (e.g., continues, combined into a whole/complete anatomical structure, see item 151 of FIG. 12B5 and item 161 of FIG. 13B). By applying the Magic Tissue Wand algorithm on to the scanned image, anatomical structure will be completed. For example, after the Tissue Wand algorithm has been applied, a vessel that was not visible in a certain part of the image, will be completed and will appear as a more continuous anatomical structure (e.g., item 161 of FIG. 13B).

Volume and or mash/polygon reconstruction—the anatomical structures that were created both with the Tissue Paint and Magic Tissue Wand algorithm and integrated with the scanned image are, for any practice consideration, an integrated part of the image. For example, the vessel that anatomical structures that originally was partial and complete, after applying the Magic Tissue Paint and Tissue Wand algorithm will become a complete anatomical structures with structure that is combined from the original scanned image and the new created structure. Furthermore, a control (check box) allows to select the new created structure and to switch between on (showing the new created structure) or off (hiding the new created structure). Additionally, an option is provided for selection to render the new created structure in a volume and or mash/polygon rendering/reconstruction.

Marked Region—A developed algorithm and software tool provides the user an interface to draw any geometric shape or free hand drawing shape in 2- or 3-dimensions (e.g., line, circle, clinic, ball etc.). The region that is included/enclosed/captured within the said geometric shape (2- or 3-dimensions) is defined as a "Marked Region". The user then, has the ability to define and assign any visual characteristics and any mechanical properties to that "marked region".

Visual characteristics; color/transparency/shading—the new created structure either or with the Magic Tissue Paint, Tissue Wand algorithm or the Marked Region can be presented in any selected visual characteristics of color that can be selected from a library of available colors, and a transparency that can be selected on any level from 0 to 100. Furthermore, the characteristics of shading and shadowing of the new created structure can be modified by tuning the characteristics of the virtual light sources. The virtual light sources characteristics includes: spherical location in space, color of the light, strength of the light, the aspect ratio, the geometric shape of the virtual source etc.

Mechanical properties—the new created structure either or with the Tissue Paint, Magic Tissue Wand algorithm or the Marked Region can be assigned with mechanical properties characteristics. That is, that a mechanical model of a specific tissue can be coupled to the new created structure and therefore, the new created structure will inherent such mechanical properties and will react, dynamically and statically according to those mechanical properties. For example, if a "soft tissue" mechanical properties where assigned to a new created structure, it will react according to a soft tissue. For example, when it will be pushed by a virtual surgery instrument, it will squeeze and reshape according to the force applied and the tissue mechanical model. Furthermore, interaction between new crated structures and other new crated structures, interaction between originally scanned structures and new crated structures and between new crated structures and originally scanned structures are seamless. The mechanical properties coefficients of any anatomical structure (stiffness, elasticity etc.) can be tuned by the user to create a tailored made mechanical behavior.

Real Time Tracking and Feedback—a system to track a real surgery instrument during the surgery. The tracking system transfers the surgery instruments location and coordination in space relative to the orientation and location of a real anatomical structure (for example, specific spot on the patient's head). The instruments' location and orientation is then sent to the surgical simulating system. Feedback is provided to the surgeon based on the patient specific simulation and the instruments' location and orientation. One example for such feedback can be; the system generates feedback to the surgeons for the type of tissue he is dissecting and alarming the surgeon in case that he dissects healthy brain tissue instead of a tumor. Additional example is that after that the surgeon applied an implement on the real anatomical structure (for example an aneurysm clip applied on an aneurysm on the real patient), the system allows the surgeon to rotate the simulated image/model that is princely oriented as the real anatomical structure based on the tracking, and observe and evaluate the location and efficacy of the placed implant.

This tracking and feedback of the real instrument can be accomplished in a number of ways, such as by using a video system to track the location and movement of the instrument and the patient features. Alternatively (or in addition to video tracking) the surgical instrument may be modified to enable tracking, such as by using GPS, accelerometers, magnetic detection, or other location and motion detecting devices and methods. Such modified instruments may communicate with the Surgical Theater using WiFi, Bluetooth, MICS, or other communications methods, for example. Interface 107 in FIG. 7 can, for example, be utilized for this feature.

Many other example embodiments of the invention can be provided through various combinations of the above described features. Although the invention has been described hereinabove using specific examples and embodiments, it will be understood by those skilled in the art that various alternatives may be used and equivalents may be substituted for elements and/or steps described herein, without necessarily deviating from the intended scope of the invention. Modifications may be necessary to adapt the invention to a particular situation or to particular needs without departing from the intended scope of the invention. It is intended that the invention not be limited to the particular implementations and embodiments described herein, but that the claims be given their broadest reasonable interpretation to cover all novel and non-obvious embodiments, literal or equivalent, disclosed or not, covered thereby.

What is claimed is:

1. A modeling system for enabling a user to perform a simulated medical procedure, said system comprising:
    one or more computers;
    a display for displaying images to the user;
    a database for storing characteristics of tissues of a particular patient;
    an image generator using one or more of said computers for executing software for generating a dynamic realistic image of the tissues of the particular patient based on the stored characteristics of the particular patient for displaying on said display, wherein said realistic image of the tissues is provided showing an appearance including shadowing and textures indicative of the tissues of the particular patient;
    the database for storing a user tool library for providing a plurality of user tool models of actual user tools used in medical procedures;
    a user interface for accepting inputs from the user for selecting one of the user tool models;
    a user tool generator using one or more of said computers for executing software for generating a realistic tool image of the selected user tool model for displaying on said display; and
    a user interface including a camera for accepting inputs from the user based on motions of the user's hands detected by images captured by the camera of the user's hands, said inputs for dynamically manipulating said selected user tool image and/or the image of the tissues for dynamically interacting with the realistic image of the tissues during the simulated medical procedure for display to the user on said display in real-time, wherein the dynamic interaction between the user tool image and the image of the tissues is displayed on said display using images with realistic visual features exhibiting realistic mechanical interactions.

2. The modeling system of claim 1, further comprising a tool to adjust the dynamic image of tissues to provide the ability to draw any geometric shape on the dynamic image of tissues.

3. The modeling system of claim 2, wherein the tool to adjust the dynamic image of tissues includes a tool to provide the ability to complete an incomplete anatomical structure of the dynamic image of tissues.

4. The modeling system of claim 2, wherein the tool to adjust the dynamic image of tissues provides the ability to modify the texture, lighting, shadow and/or shading of a portion of the dynamic image of tissues.

5. The modeling system of claim 2, wherein the tool to adjust the dynamic image of tissues includes a tool to provide the ability to command the tool to interact with one or more portions of the dynamic image of tissues.

6. The modeling system of claim 2, wherein the tool to adjust the dynamic image of tissues includes a tool to provide the ability to select elements of a model of the tool and/or the dynamic image of tissues for removal from the displayed image.

7. The modeling system of claim 2, wherein the tool to adjust the dynamic image of tissues includes a tool to provide the ability to reposition objects in the displayed image by selecting the objects and dragging the objects to a desired position for display in the image.

8. The modeling system of claim 2, wherein the tool to adjust the dynamic image of tissues includes a tool to provide the ability to enhance and integrate anatomical structure in the dynamic image.

9. The modeling system of claim 2, wherein the tool to adjust the dynamic image of tissues includes a tool to provide the ability to a draw any geometric shape for adding to the dynamic image of tissues.

10. The modeling system of claim 1, further comprising:
    a database for storing a library of a plurality of models of different implants; and
    a user interface for selecting one implant model from said plurality of models for use with said user tool model for dynamically interacting with said image of tissues.

11. The modeling system of claim 1, wherein a tool to adjust the dynamic image of tissues includes tools to provide the abilities to:
  draw any geometric shape on the dynamic image of tissues;
  complete an incomplete anatomical structure of the dynamic image of tissues; or
  modify the texture, and/or lighting of a portion of the dynamic image of tissues.

12. The modeling system of claim 1, wherein the inputs from the user based on motions of the user's hands are configured to track the motions of an actual surgical instrument being used by the user with the particular patient, such that said motions are used for dynamically manipulating said selected user tool image and/or the image of the tissues for dynamically interacting with the realistic image of the tissues during the simulated medical procedure for display to the user on said display in real-time.

13. The modeling system of claim 12, wherein the motions of an actual surgical instrument are tracked using a GPS receiver, an accelerometer, a magnetic detection device, and/or a camera.

14. A modeling system for enabling a user to perform a simulated medical procedure, said system comprising:
  one or more computers;
  a display for displaying images to the user;
  a database for storing physical characteristics of the tissues of a particular patient;
  an image generator using one or more of said computers for executing software for generating a dynamic realistic image of the tissues of the particular patient for displaying on said display, wherein said realistic image of the tissues is provided showing an appearance including shadowing and textures indicative of the tissues of the particular patient;
  a database comprising a user tool library for providing a plurality of user tool models of actual user tools used in medical procedures;
  a user interface for accepting inputs from the user for selecting one of the user tool models;
  a user tool generator using one or more of said computers for executing software for generating a realistic tool image of the selected user tool model for displaying on said display;
  a user interface for accepting inputs from the user, said inputs for dynamically manipulating said selected user tool image for dynamically interacting with said realistic image of the tissues during the simulated medical procedure for display to the user on said display in real-time;
  a user interface including a camera for accepting inputs from the user based on motions of the user's hands, said inputs for dynamically manipulating said selected user tool image and/or the image of the tissues for dynamically interacting with the realistic image of the tissues during the simulated medical procedure for display to the user on said display in real-time, wherein
  the dynamic interaction between the user tool image and the image of the tissues is displayed on said display using images with realistic visual features exhibiting realistic mechanical interactions; and
  a user interface providing a tool to adjust the dynamic image of the tissues displayed on said display by adding or modifying features of said tissues for display to compensate for anatomical structures that are in the actual biological tissue of the particular patient but are missing from the dynamic image of tissues originally displayed such that the dynamic image of tissues displayed are subsequently displayed on the display with the added or modified features, wherein
  the dynamic interaction between the user tool image and the image of the tissues is displayed on said display providing realistic visual features exhibiting realistic mechanical interactions based on the stored physical characteristics.

15. The modeling system of claim 14, wherein the tool to adjust the dynamic image of tissues includes a tool to provide the ability to draw any geometric shape on the dynamic image of tissues.

16. The modeling system of claim 14, wherein the tool to adjust the dynamic image of tissues includes a tool to provide the ability to complete an incomplete anatomical structure of the dynamic image of tissues.

17. The modeling system of claim 14, wherein the tool to adjust the dynamic image of tissues includes a tool to provide the ability to modify the texture, lighting, shadow and/or shading of a portion of the dynamic image of tissues.

18. The modeling system of claim 14, wherein said medical images of the particular patient include an image of an aneurysm, and wherein said dynamic image includes an image of the aneurysm, and further wherein said user tool includes an aneurysm clip applier for applying an aneurysm clip model for dynamically interacting with the image of tissues.

19. The modeling system of claim 14, wherein the tool to adjust the dynamic image of tissues includes a tool to provide the ability to command a tool to interact with one or more portions of the dynamic image of tissues.

20. The modeling system of claim 14, wherein the tool to adjust the dynamic image of tissues includes a tool to provide the ability to select elements the tool model and/or the dynamic image of tissues for removal from the displayed image.

21. The modeling system of claim 14, wherein the tool to adjust the dynamic image of tissues includes a tool to provide the ability to reposition objects in the displayed image by selecting the objects and dragging the objects to a desired position for display in the image.

22. The modeling system of claim 14, further comprising:
  a database for storing a library of a plurality of models of different implants; and
  a user interface for selecting one implant model from said plurality of models for use with said user tool model for dynamically interacting with said image of tissues.

23. The modeling system of claim 14, wherein a tool to adjust the dynamic image of tissues includes tools to provide the abilities to:
  draw any geometric shape on the dynamic image of tissues;
  complete an incomplete anatomical structure of the dynamic image of tissues; or
  modify the texture, and/or lighting of a portion of the dynamic image of tissues.

24. The modeling system of claim 14, further comprising a user interface that can track the motions of an actual surgical instrument being used by the user with the particular patient, such that said motions are used for dynamically manipulating said selected user tool image and/or the image of the tissues for dynamically interacting with the realistic image of the tissues during the simulated medical procedure for display to the user on said display in real-time.

25. The modeling system of claim 24, wherein said user interface that can track the motions of an actual surgical instrument includes a GPS receiver, an accelerometer, a magnetic detection device, or a camera.

26. A modeling system for enabling a user to perform an actual medical procedure, said system comprising:
   one or more computers;
   a display for displaying images to the user;
   a database for storing characteristics of tissues of a particular patient obtained from imaging of the particular patient taken in advance of the procedure;
   an image generator using one or more of said computers for executing software for generating a dynamic realistic image of the tissues for particular patient for displaying on said display, wherein said realistic image of the tissues is provided showing an appearance including shadowing and textures indicative of actual tissues and is based on the characteristics of the tissues of the particular patient stored in the database;
   a database for storing a user tool library for providing a plurality of user tool models of actual user tools used in medical procedures;
   a user interface for accepting inputs from the user for selecting one of the user tool models;
   a user tool generator using one or more of said computers for executing software for generating a realistic tool image of the selected user tool model for displaying on said display; and
   a user interface including a motion detecting device that can track the motions of an actual surgical instrument being used by the user with the particular patient during the actual medical procedure, such that said motions are used for dynamically manipulating said selected user tool image and/or the image of the tissues for dynamically interacting with the realistic image of the tissues and for providing different views of the tissues according to the characteristics of the tissues of the particular patient based on the tracked motions of the surgical instrument during the medical procedure for display to the user on said display in real-time.

27. The modeling system of claim 26, wherein said motion detection device includes a GPS receiver, an accelerometer, a magnetic detection device, and/or a camera.

28. The modeling system of claim 26, further comprising a user interface including a camera for accepting inputs from the user based on motions of the user's hands, said inputs for dynamically manipulating said selected user tool image and/or the image of the tissues for dynamically interacting with the realistic image of the tissues during the simulated medical procedure for display to the user on said display in real-time, wherein the dynamic interaction between the user tool image and the image of the tissues is displayed on said display using images with realistic visual features exhibiting realistic mechanical interactions.

* * * * *